(12) United States Patent
Tabata et al.

(10) Patent No.: US 7,605,231 B2
(45) Date of Patent: Oct. 20, 2009

(54) GELATIN DERIVATIVES AND HIGH-MOLECULAR MICELLE COMPRISING THE DERIVATIVES

(75) Inventors: Yasuhiko Tabata, 8-16, Biwadai 3-chome, Uji-shi, Kyoto 611-0024 (JP); Koji Sakaguchi, Ibaraki (JP); Shinji Tanaka, Ibaraki (JP)

(73) Assignees: Yasuhiko Tabata, Uji-shi, Kyoto (JP); NOF Corporation, Tokyo (JP)

( * ) Notice: Subject to any disclaimer, the term of this patent is extended or adjusted under 35 U.S.C. 154(b) by 0 days.

(21) Appl. No.: 10/973,846

(22) Filed: Oct. 25, 2004

(65) Prior Publication Data

US 2005/0147661 A1 Jul. 7, 2005

Related U.S. Application Data

(63) Continuation of application No. PCT/JP03/05343, filed on Apr. 25, 2003.

(30) Foreign Application Priority Data

Apr. 26, 2002 (JP) ............................. 2002-127035

(51) Int. Cl.
*A61K 38/00* (2006.01)
(52) U.S. Cl. ...................... 530/354; 514/2; 977/773
(58) Field of Classification Search ...................... None
See application file for complete search history.

(56) References Cited

U.S. PATENT DOCUMENTS

| 6,200,590 | B1 * | 3/2001 | Eley | 424/433 |
| 7,067,144 | B2 * | 6/2006 | Demopulos et al. | 424/423 |
| 2003/0083389 | A1 * | 5/2003 | Kao et al. | 516/98 |
| 2004/0137179 | A1 * | 7/2004 | Matsuda et al. | 428/36.1 |

FOREIGN PATENT DOCUMENTS

| EP | 1 027 888 A2 | 8/2000 |
| JP | 5-43453 A | 2/1993 |
| JP | 8-325160 | 12/1996 |
| JP | 9-103479 A | 4/1997 |
| JP | 2001-172203 A | 6/2001 |
| WO | WO 98/20755 A1 | 5/1998 |

OTHER PUBLICATIONS

Kim et al., J. of Controlled Release, 1998, 51:13-22.*
Kim and Byun, "Preparation and characterizations of self-assembled pegylated gelatin nanoparticles", Biotechnol. Bioprocess Eng. 4: 210-214 (1999).*
Kim and Byun, "Controlled release of All-trans-retinoic acid from pegylated gelatin nanoparticles by enzymatic degradation", Biotechnol. Bioprocess Eng. 4: 215-218 (1999).*
T. Kushibiki et al, "Gelatin to Polyethylene glycol to kara naru Bunshi Shugotai no Chosei", *Drug Delivery System*, vol. 17, No. 3, p. 263 (May 10, 2002).
G. Kaul et al, "Long-Circulating Poly(Ethylene Glycol)-Modified Gelatin Nanoparticles for Intracellular Delivery", *Pharmaceutical Research*, vol. 19, No. 7, pp. 1061-1067 (Jul. 2002).
J. Zimmerman et al, "Novel hydrogels as supports for in vitro cell growth: . . . ", *Biomaterials*, vol. 23, No. 10, pp. 2127-2134 (May 2002).
T. Morita et al, "Preparation of gelatin micro-particles by co-lyophilization with poly(ethylene glycol): . . . ", *Intl. Journal of Pharmaceutics*, vol. 219, No. 1-1, pp. 127-137 (May 2001).
PCT International Preliminary Examination Report PCT/IPEA/401 (English language translation) in the parent application PCT/JP2003/005343 (4 pages).

* cited by examiner

*Primary Examiner*—Anand U Desai
(74) *Attorney, Agent, or Firm*—Frishauf, Holtz, Goodman & Chick, P.C.

(57) ABSTRACT

The present invention relates to a gelatin derivative having an organic compound as a graft chain and a high-molecular weight micelle containing the gelatin derivative. As the organic compound, a low molecular weight compound such as succinic acid, ethylenediamine, etc., or a high-molecular weight compound such as polyethylene glycol, polylactic acid, etc. can be used. The high-molecular weight micelle can be used as a pharmaceutical composition excellent in control of sustained release or targeting property by carrying it on a drug, etc. Also, the gelatin derivative can be an excellent adhesion preventing membrane by crosslinking it.

6 Claims, 19 Drawing Sheets

Fig.17
(A)
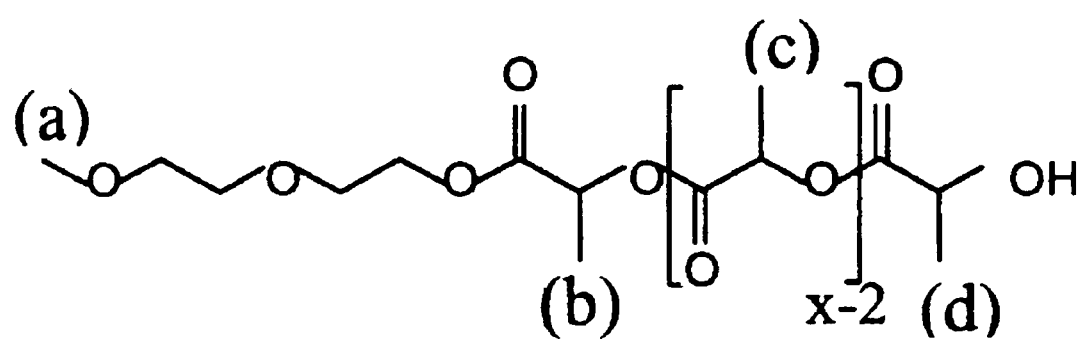
(B)
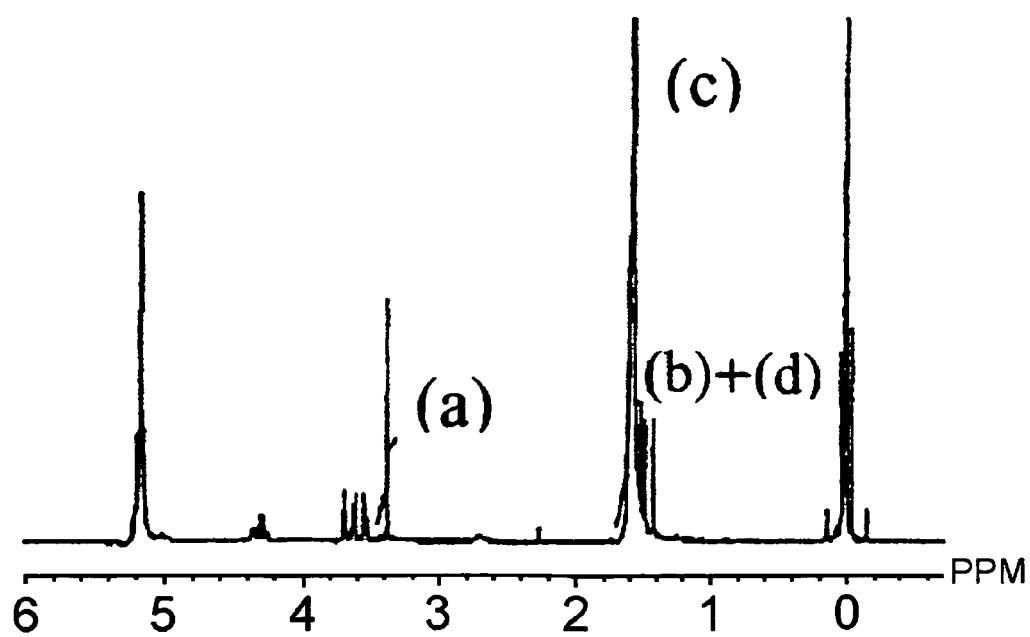

Fig.19
(A)
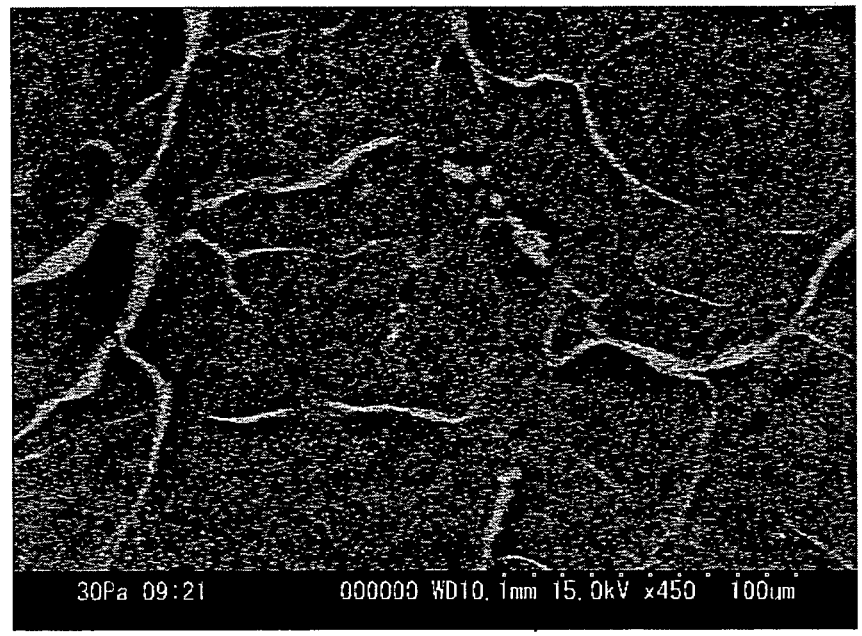
(B)
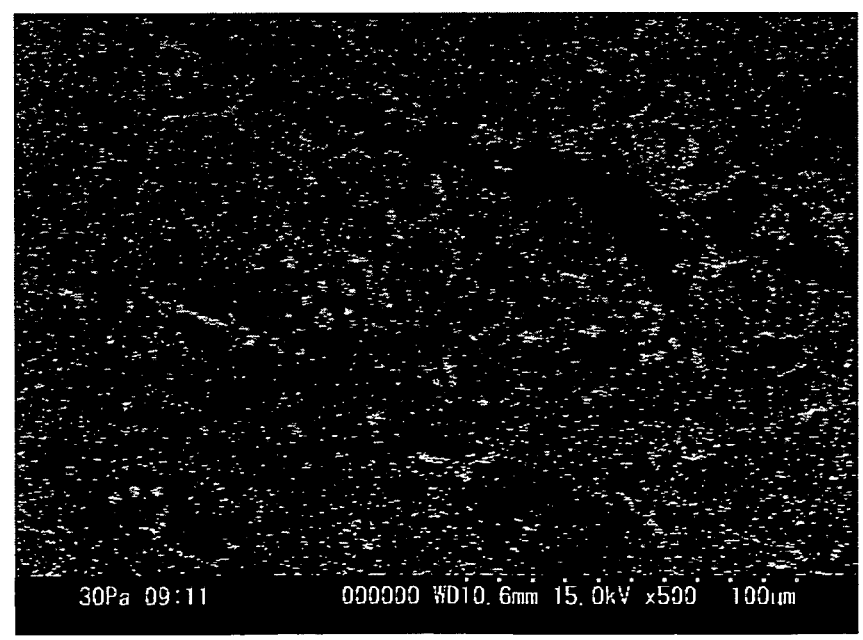

GELATIN DERIVATIVES AND HIGH-MOLECULAR MICELLE COMPRISING THE DERIVATIVES

This application is a continuation application of International Application PCT/JP03/05343 filed Apr. 25, 2003.

TECHNICAL FIELD

The present invention relates to a gelatin derivative, a high-molecular weight micelle comprising the derivative, a high-molecular weight micelle complex prepared by supporting a second component substance on the micelle and a pharmaceutical composition containing the high-molecular weight micelle complex.

TECHNICAL BACKGROUND

Drugs act in such a way that drug molecules taken from the mouth or injected reach to a specific cell in the body and stimulate the cell. However, practically only a part of the drug administered can reach to a region to be acted, and thereby most of the drug is evacuated as it is from the body or it always acts normal cells to cause side-effects.

Therefore, it is ideal that a necessary amount of drugs can be sent to necessary cells at a necessary time. In the study for controlling the drug effect by utilizing various materials for attaining the object, there is a drug delivery system (DDS). Until now, investigation and development have been carried out by various approaches.

The objects of DDS are to release drugs over a definite period of time at a definite rate (formation of sustained release), to prolong the life of a drug having a short half-life in vivo, to promote the absorption of drugs from the keratin of the skin or the mucous membrane tissue, and to drug targeting of aiming at only a target cell. Among the objects, the sustained release of drugs has widely been attempted conventionally.

For example, the formation of sustained release functions of drugs from hydrogel of in vivo absorption high-molecular weight compounds such as polylactic acid carriers etc., are studied (Advanced Drug Delivery Review, 2002, 43, 3-12). For the second object, there are a report on modification of drugs by water-soluble polymers, PEG etc. (Pharmazie, 2002 January 57(1), 5-29) and a report of utilizing PEG-modified liposome etc. (JP-A-11 (1999)-171771, Nippon Rinsho 1998 March, 56(3), 632-637). For the drug targeting, there are attempts to use polymers, antibody or liposome (Crit Rev Ther Drug Carrier Syst., 1987, 3(3), 233-261).

In the formation of sustained release functions of drugs by the use of hydrogel, the formation of sustained release is regulated by self-diffusion of a drug in an aqueous phase in the hydrogel. Therefore, it is difficult to control sustained release patterns, for example, it is very difficult to perform the formation of sustained release functions of a water-soluble drug over 3 or more days although it depends on a molecule size of the drug or its water solubility. In the diffusion-controlled drug sustained release system, in the case that the hydrogel which is a carrier for the formation of sustained release has a small size capable of administration with injection, the hydrogel carrier has a large surface per volume and a drug is released for a short period of time so that it is more difficult to perform the formation of sustained release of the drug. Further, in the case that the hydrogel carrier has a nanometer size capable of applying for intravenous administration, it is practically impossible to perform the formation of sustained release of a drug.

For sustained release of a water-soluble drug such as protein, gene etc., from the hydrogel, it is reported that the drug is physically fixed inside a gel and the formation of sustained release of the drug can be attained by water solubilization of the drug accompanied with decomposition of the gel carrier and the formation of sustained release of the drug can be continued over 3 or more days (Adv. Drug Deliv. Rev., 1998 May 4, 31(3) 287-301). In this system, further, by the method of dispersing the hydrogel-constituting polymer aqueous solution in oil and thereby preparing hydrogel fine particles, the size of the fine particles is successfully decreased to be several ten micrometers. However, the size limit is several micrometers by the dispersing method for preparing these hydrogels. Even if such fine particles can be prepared, there is a further problem caused that the hydrogels are aggregated mutually.

The method of utilizing liposome can solve the problems on size and aggregation, but it is difficult to control the period of sustained release because of low stability in the body.

Furthermore, a method of using a high-molecular weight micelle comprising a copolymer of a hydrophobic polyamino acid and a hydrophilic polymer (Japanese Patent No. 2777530) is disclosed. This method can also solve the problems on size and aggregation, but it has a problem of controlling the sustained release properties of a drug because the formation of sustained release of a drug from the high-molecular weight micelle is due to diffusion of the drug contained in the micelle.

DISCLOSURE OF THE INVENTION

The present inventors have been earnestly studied to develop a system in which it has a size of a nanometer order without causing aggregation to each other and is capable of controlling sustained release of a drug, and as a result, they have found that a stable high-molecular weight micelle is formed by utilizing and derivatizing gelatin which is capable of interacting with various drugs and is biologically resolving or degradable in a living body, and further a more stable micelle complex is formed by supporting a second component substance such as drugs etc., on this micelle and moreover, it is useful as a carrier of the drugs for solving the above problems. Thus, the present invention has been accomplished.

That is, the present invention relates to a gelatin derivative prepared by covalently bonding an organic compound to a functional group such as an amino group, a hydroxyl group or a carboxyl group of gelatin molecules, a high-molecular weight micelle comprising the gelatin derivative preferably having a particle diameter of from 10 to 1000 nm, and a high-molecular weight micelle complex prepared by supporting a second component substance on the micelle and further relates to a medical composition containing the high molecule micelle complex.

As the organic compound used for the derivatization of gelatin molecules, any one may be used regardless of its molecular weight, hydrophilic property, hydrophobic property, charge or non-charge as far as the organic compound can covalently bonded with a functional group such as an amino group, a hydroxyl group or a carboxyl group of the gelatin. These organic compounds are covalently bonded with a functional group such as an amino group, a hydroxyl group or a carboxyl group of the gelatin and thereby a gelatin derivative is prepared.

As the organic compound used for the derivatization of gelatin, it is possible to use organic compounds having a low or high-molecular weight.

The low molecular weight organic compound has a molecular weight of preferably not more than 500. In order to introduce an alkane, an alkene or an alkyne residue each having 1 to 24 carbon atoms, the low molecular weight organic compound may include their derivatives containing a primary, secondary or tertiary hydroxyl group, a primary, secondary or tertiary amino group, a carboxyl group, a sulfuric acid group, a phosphoric acid group, a thiol group, an acid amide group, an aromatic group or a heterocyclic ring, and, for example, succinic anhydride, succinic acid, and an alkane, an alkene or an alkyne each having 1 to 24 carbon atoms, which have a halogen, a hydroxyl group, an amino group, a carboxyl group or a phosphoric acid group at their one end or both ends, and benzene derivatives thereof. Specific examples thereof are alkane chlorides or bromides (e.g. ethyl chloride, ethyl bromide, octyl chloride, hexyl chloride, isobutyl chloride, etc.), alkyl alcohols (e.g. propyl alcohol, octyl alcohol, isobutyl alcohol, etc.), alkyl amines (e.g. ethylamine, propylamine, isobutylamine, etc.), alkyl diamines (e.g. ethylenediamine, propanediamine, hexamethylenediamine, spermine, spermidine, etc.), alkyl diols (e.g. ethylene glycol, propylene glycol, etc.), aminoalkyl alcohols (e.g. 3-amino-1-propanol), alkyl carboxylic acids (e.g. acetic acid and butyric acid), alkyl carboxylic acid chlorides or bromides (e.g. chloroacetic acid), aminoalkyl carboxylic acids (e.g. aminoacetic acid and aminobutyric acid), hydroxyalkyl carboxylic acids (e.g. glycolic acid), alkyl dicarboxylic acids (e.g. ethylene dicarboxylic acid), alkyl phosphoric acids (e.g. triethyl phosphoric acid), alkyl phosphoric acid chlorides or bromides and aminoalkyl phosphoric acids.

Examples of the high-molecular weight organic compound may include various kinds of synthetic high-molecular compounds, natural high-molecular weight compounds and the derivative thereof as described above.

The synthetic high-molecular weight compounds used for gelatin derivatization may include low molecular weight oligomers and synthetic high-molecular weight compounds, for example, polyalkylene glycols (e.g. polyethylene glycol (PEG), polypropylene glycol, polybutylene glycol and copolymers thereof), poly(meth)acrylamides, poly(meth)acrylic acids, poly(meth)acrylates, polyallylamines, polyvinyl pyrrolidones, polyvinyl alcohols, polyvinyl acetates, biodegradable polyesters (e.g. polylactic acid, poly-ε-caprolactam, succinate polymers and polyhydroxyalkanoate), polyglycolic acids, polymalic acids, polydioxanones and polyamino acids; and derivatives thereof. Of these compounds, examples of the polyamino acid may include acidic, basic, non-charged hydrophilic or hydrophobic amino acid homopolymers and copolymers, such as poly-α-glutamic acid, poly-γ-glutamic acid, polyasparagic acid, poly-lysine, polyarginine, polyornithine, polyserine, etc. Examples of the succinate polymer may include polyethylene succinate, polybutylene succinate, polybutylene succinate adipate, etc. Examples of the polyhydroxyalkanoate may include polyhydroxypropionate, polyhydroxybutylate, polyhydroxyparrilate, etc.

Examples of the natural high-molecular weight compounds utilized for gelatin derivatization may include proteins, polysaccharides, nucleic acids, etc., and further include derivatives thereof and copolymers with the above synthetic high-molecular weight compounds. Examples of polysaccharide may include dextran, pullulan, mannan, curdlan, xanthan, alginic acid, hyaluronic acid, agarose, etc.

The usable high-molecular weight compounds have a molecular weight, which is not particularly limited, of for example, from 500 to 1,000,000, preferably 1000 to 100,000.

Further, the gelatin derivatives may include not only at least one of the above-mentioned low-molecular weight compounds and the high-molecular weight compounds but also two or more kinds of compounds covalently bonded with gelatin regardless of the introducing rate or mixing ratio thereof. For example, it is possible to covalently bond both of the low-molecular weight compounds such as succinic acid or ethylenediamine and the high-molecular weight compounds such as PEG derivatives, etc., with gelatin or it is possible to covalently bond both of the hydrophobic polymer such as polylactic acid, etc., and the high-molecular weight compounds such as PEG derivative, etc., with gelatin. In this case, the proportion of the polylactic acid and the PEG derivative covalently bonded with gelatin can be appropriately selected in accordance with the second component substance for supporting. Further, the kind of the organic compounds used for the gelatin derivatization can be also appropriately selected in accordance with the second component substance for supporting.

Particularly preferred examples of the residue derived from the high-molecular weight compounds are derivative of PEG having a reactive functional group at only one end from the view point of ease of defining the chemical reaction mode and ease of characterization of the synthetic compounds, namely polyethylene glycol derivatives having a chemical structure represented by the following formula (1);

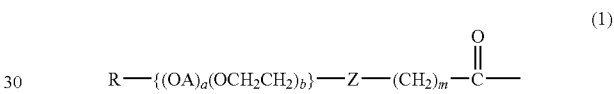

(1)

(wherein R is a straight or branched alkyl group or alkenyl group both having 1 to 24 carbon atoms, OA is an oxyalkylene group having 3 to 4 carbon atoms, the oxyalkylene group and an oxyethylene group may be added in the block state or randomly. a and b are respectively an average addition mole number of oxyalkylene group and that of the oxyethylene group, and satisfy the following formulas; $0 \leq a \leq 200$, $4 \leq b \leq 2000$, and $a/(a+b) \leq 0.5$. Z is O or OC(O), and m is an integer of 0 to 3.).

In the formula (1), R is a straight or branched alkyl group or alkenyl group both having preferably 1 to 12 carbon atoms, more preferably 1 to 6 carbon atoms.

Examples of R are alkyl groups such as methyl group, ethyl group, propyl group, butyl group, isobutyl group, sec-butyl group, tert-butyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, henicosyl group, docosyl group, tricosyl group, tetracosyl group, isostrearyl group, etc., and alkenyl groups such as tetradecenyl group, hexadecenyl group, octadecenyl group, etc. These groups may be used singly or in combination of two or more kinds.

Examples of the oxyalkylene group of OA may include oxypropylene group, oxybutylene group and oxytetramethylene group.

a is preferably from 0 to 200, more preferably 0 to 100, most preferably 0 to 50. b is preferably from 4 to 2000, more preferably 10 to 1000, most preferably 50 to 200. a/(a+b) is preferably from 0 to 0.5, more preferably 0 to 0.3, most preferably 0 to 0.1. When the value of a/(a+b) is over 0.5, the hydrophilic property is lowered.

m is preferably from 1 to 3.

Z is preferably OC(O).

The lactic acid used for synthesis of polylactic acid may be any of D-lactic acid, L-lactic acid or a mixture of D-lactic acid and L-lactic acid, and further lactide, which is a dimer of lactic acid, can be also used as a raw material. As the polymerization method thereof, any of known methods such as condensation polymerization method, ring opening polymerization method, etc., can be employed.

As the gelatin, it is possible to use any of various kinds of gelatins including human genetic recombinant type gelatins regardless of the type of collagen, the original animal of collagen or the collected internal body site, each of which is a starting material of the gelatin. Examples of the gelatin may include alkali treated gelatin having an isoelectric point of about 5, acid treated gelatin having an isoelectric point of about 9, etc.

Particularly preferred examples of the gelatin derivative are gelatin derivatives having a graft chain represented by the above-mentioned formula (1) in a part or all of amino groups and hydroxyl groups of the gelatin molecules.

PEG having a reactive functional group at only one end represented by the above-mentioned formula (1) can be grafted on gelatin using a conventionally known method.

The rate of introducing the organic compound to gelatin molecules with covalent bonding varies depending on the affinity of the second component substance to be included with the gelatin derivative, and further the rate is preferably from 5 to 100%, more preferably 50 to 80% based on all of the function groups such as amino group, hydroxyl group, carboxyl group, etc., of the gelatin molecules. In particular, the organic compound is introduced in preferably at least 50%, most preferably not less than 80% of all of the amino groups of the gelatin molecules.

The high-molecular weight micelle used in the present invention means both molecular aggregate containing the above-mentioned gelatin derivatives and molecular aggregate formed by the interaction of the gelatin derivatives and the second component substance. When it means the latter only, the high-molecular weight micelle is a high-molecular weight micelle complex.

The high-molecular weight micelle containing the gelatin derivatives has an average particle diameter of, for example, from 10 to 1000 nm, preferably 20 to 500 nm, and particularly preferably 20 to 300 nm.

Because the micelle of the present invention has very small CMC, it is considered that even if in vivo intravenous administration that the micelle is administered into the body and then rapidly diluted, the stable micelle is formed in the blood. Furthermore, because of the micelle of the present invention having a small average particle diameter different from particles having a diameter of μm order, it is also considered that the administration thereof can perform incorporation removal from the blood by the reticuloendothelial system after the administration in the blood, or embolus of the blood vessel can be avoided, and further, when the micelle reaches to the depths of the lung after the endotracheal administration, the dosage sufficient for curing can be administrated by an extremely minute amount of the solution.

The present invention further relates to a high-molecular weight micelle complex prepared by supporting the second component substance on the high-molecular weight micelle containing the gelatin derivatives. In this high-molecular weight micelle complex, the gelatin and the substances included conduct stable interaction so that the substances are not released from the complex in a usual aqueous solution. However, for example, when the complex is disintegrated due to decomposition of the gelatin caused by an enzyme, etc, the substances are released from the complex with the disintegration. This mechanism attains the formation of sustained release of the substances from the complex carrier having a size of nanometer order without occurrence of aggregation.

Examples of the second component substance used in the present invention may include drugs, substances having medical effects such as metals, ceramics, organic compounds, etc., and substances for working as a labeled compound.

The structure of the high-molecular weight micelle of the present invention, which varies depending on the composition of the gelatin derivatives or the kind of the second component substances, comprises a gelatin part as a core and a derivative part covalently bonded with the gelatin as a shell, or contrarily comprises a gelatin part as a shell and a derivative part covalently bonded with the gelatin as a core. In the former structure, the high-molecular weight micelle is further stabilized by the interaction of the second component substance and the gelatin. The latter structure is, for example, the case of conducting derivatization of the gelatin by a hydrophobic compound, and in the inside, the core is formed by association of the hydrophobic compounds and the gelatin part is exposed in the shell part. In this case, a high-molecular weight micelle having the substance capable of interaction with the gelatin in the high-molecular weight micelle surface layers can be prepared. Further, in the latter case, the hydrophobic substance can be included inside the high-molecular weight micelle and the latter case is effective as a solubilizing method for slightly soluble substances, Additionally, the drugs are included inside the micelle so that the drugs can be protected by hydrolysis of acids or enzymes. This property can be utilized as an entric coating agent at the time of the oral administration. Namely, the present micelle system can realize an emulsion type entric coating technique of drugs. The stabilization of the substances included in the micelle is also useful for cosmetic additives such as skin whitening cosmetic agents, UV protecting agents, etc.

Examples of the drugs for the second component substance may include various kinds of low-molecular weight and high-molecular weight drugs regardless of hydrophilic property, hydrophobic property, electric charge or non-electric charge. Specific examples thereof are anticancer agents such as adriamycin, paclitaxel, camptothecine, daunomycine, mitomycine, methotrexate, cisplatin, etc., analgesic and antiphlogistic agents such as indometacine, etc., central nervous system drugs, peripheral nervous system drugs, allergy drugs, circulatory system drugs, respiratory organ drugs, disgestive system drugs, hormone drugs, metabolic medicines, antibiotics, chemotherapeutic drugs, peptide drugs such as insulin, calcitonin, LHRH, etc., protein drugs such as chemokine, cytokine, cell growth factors, interferon, interleukin, etc., nucleic acid drugs such as DNA, RNA, antisense DNA, decoy gene, etc.

Examples of the cell growth factors may include those generally called as cell growth factors, such as bFGF (basic fibroblast growth factor), aFGF (acidic fibroblast growth factor), PDGF (platelet-derived growth resistance factor), TGF (transforming growth factor)-$\beta 1$, VEGF (vascular endothelial growth factor), HGF (hepatocytes growth factor), etc., and substances having activity capable of causing growth of cells constituting blood vessels such as blood vessel endothelial cell, smooth muscle cell, etc., or their peripheral cells, such as interleukin, cytokine, chemokine, bioactive peptides, etc.

Examples of the second component substances other than the drugs are cosmetic additives, metals, inorganic compounds, etc. Examples of the metals are gadolinium, magnesium, titanium, platinum, copper, zinc, etc.

The inorganic compounds are not specifically limited, and examples thereof may include compounds comprising ceramics such as hydroxyapatite, α or β-tricalcium phosphate, calcium phosphate, etc., and a transition element and a typical element.

The cosmetic additives are not specifically limited, and examples thereof may include substance for adding cosmetics as skin-whitening agents, UV-ray absorbers or inorganic substances, and substance for adding properties such as whitening or UV-ray cutting to cosmetics.

The organic compounds as the second component substances are not specifically limited, and examples thereof may include fullerene, carbon nano-tube, and derivatives thereof, compounds thereof with other elements, and labeling compounds such as organic dye compounds, organic fluorescent compounds, radio isotope, etc.

The present invention also relates to pharmaceutical compositions containing the above-mentioned high-molecular weight micelle complex, diagnosis compositions and a drug delivery system. Various pharmaceutical compositions, etc., are prepared from the second component substances included in the high-molecular weight micelle.

The pharmaceutical compositions of the present invention can contain usual excipients and additives in the form of solutions, syrups or injectable solutions. Further, the pharmaceutical compositions of the present invention can be administered via the oral route, percutaneous route, lung route, mucous membrane route, subcutaneous route, intracutaneous route, intramuscular route, intravenous route, etc.

Furthermore, the present invention relates to an anti-adhesive membrane containing the above-mentioned gelatin derivatives. The anti-adhesive membrane can be prepared, for example, by a method of gelation of the gelatin derivatives or a method of gelation of the gelatin derivatives and then crosslinking by heating or using a crosslinking agent such as glutaric aldehyde, and the latter method is preferred. It is also possible to add anti-adhesive properties to other membrane materials by coating or laminating the above-mentioned gelatin derivatives on the surface of the other membrane materials. The gelatin derivatives also have properties of depressing adhesion of macrophage, etc., which are inflammatory cells. Therefore, using the membrane of the gelatin derivatives or in combination with other membranes as mentioned above, they can be used as a biocompatibility material incapable of causing foreign matter actions or inflammatory actions, or can also be used as a base material capable of endowing biocompatibility properties to materials.

Examples of additives optionally added to the anti-adhesive membrane may include hemostatics capable of controlling blood coagulation such as fibrinogen, fibrin, trasylol, aprotinin, thrombin, etc.; fibrinolysins such as tissue plasminogen activator, plasminogen activator analogues, streptokinase, urokinase, urokinase etc.; drugs for preventing from adhesion after operation or five monosaccharides such as thrombin inhibitor, kimase inhibitor, etc.; glycosaminoglycans for controlling physical properties of a structure material such as dermatane sulfate, chodroitin sulfate, heparan sulfate, heparin, hyaluronic acid, etc.; natural polymers such as acidic oxidized cellulose, alginic acid, etc.; in vivo absorbing synthetic polymers such as polyglycolic acid, polylactide, polypeptide, etc.; calcium channel blocker; steroids for decreasing inflammation or throbbing pain after operation such as hydrocortisone, clobetasone butyrate, betamethasone valerate, propionic acid butylate hydrocortisone, etc.; non-steroid anti-inflammatory agents such as aspirin, indometacin, sulindac, diclofenac, fenbufen, naproxen, ketoprofen, loxoprofen, piroxicam, mefenamic acid, tiaramide, etc.; growth factors derived from epidermis for accelerating wound healing; growth factors derived from platelet and the like.

BRIEF DESCRIPTION OF DRAWINGS

FIG. 17 is a diagram showing a structural formula (A) of $LLA_0$ and a $^1$H-NMR spectrum (B).

FIG. 19 is an electron microscopic photograph of a surface of a specimen for evaluating macrophage adhesive ability in Example 30, where (A) shows the photograph of a specimen prepared from crosslinked PEG-grafted gelatin and (B) shows the photograph of a specimen prepared from crosslinked gelatin.

BEST MODE FOR CARRYING OUT THE INVENTION

Figure 1:
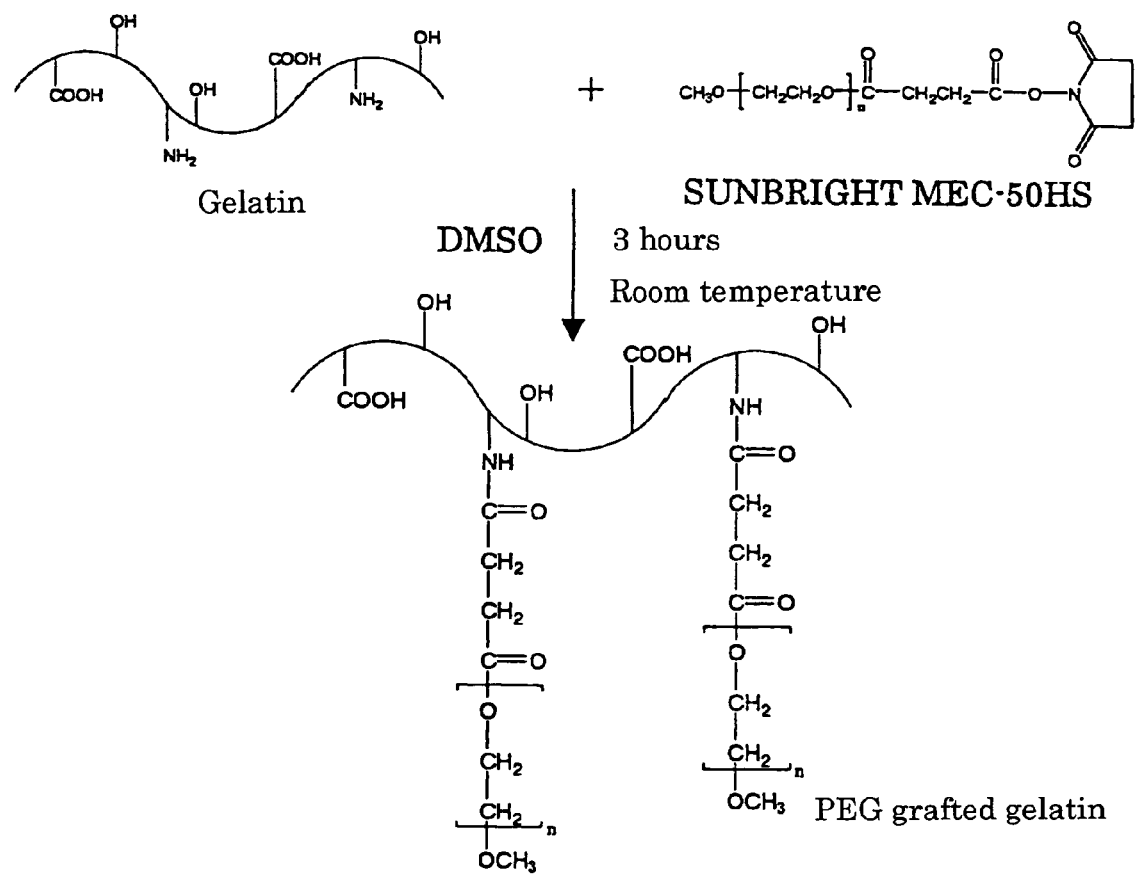
FIG. 1 is a diagram showing one synthetic scheme of PEG-grafted gelatin according to the present invention.

The gelatin derivatives of the present invention can be prepared by allowing gelatin dissolved in an appropriate solvent to chemically react with an organic compound dissolved in an appropriate solvent, an organic compound derivative or their activated derivatives.

Various conventionally known reaction methods known in general organic chemistry can be utilized for the chemical bonding reaction used for preparing derivatives. However, excessive reaction conditions causing cut of gelatin molecular chains should be not employed. For example, it is preferred to employ moderate reactions used for chemical modification reaction of protein (Bioconjugate Techniques, G. T. Hermanson, Academic Press, Inc. NY. 1996).

For example, in the case that PEG which is one of hydrophilic polymer compounds is chemically bonded to amino groups of gelatin, it is preferred to use activating derivatives having reactivity to amino groups or to conduct coupling reaction with a condensing agent. Examples of the activating derivatives include activating esters, carbodiimidazol derivatives, acid anhydride derivatives, acid chloride derivatives, aldehyde derivatives, etc.

The derivatization of the functional groups of the gelatin molecules other than amino groups can be conducted by the same method as one in the amino groups or a method known for those skilled in the art.

Preferred examples of the activating derivatives of the hydrophilic polymer compound for derivatizing amino groups are succinimidyl sccuinate derivatives of PEG represented by the following formula (2):

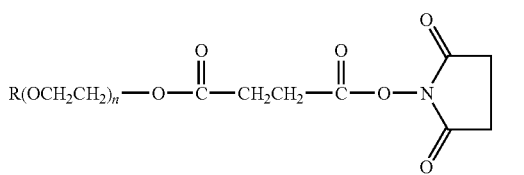

(2)

(wherein R is the same as those in the formula (1), n is from 4 to 2000, preferably 20 to 1000, more preferably 40 to 500.).

Examples of the solvent capable of dissolving the gelatins, the hydrophilic polymer compounds or their activating derivatives may include dimethylsulfoxide (DMSO), dimethylformamide (DMF), water, etc.

As the method of introducing biodegradable polyesters such as polylactic acid derivatives to the gelatins, it can be carried out by the following methods.

Examples of the method of grafting the lactic acid to the gelatins may include a method of grafting with direct addition polymerizing lactic acid or lactide and a method of grafting after polymerizing the lactic acid. The method of grafting the polymerized polylactic acid is preferred from the view point of easiness of controlling the grafting ratio because the gelatin derivatives of the present invention have a possibility such that the grafting ratio is appropriately changed by the second components. As the method for grafting the polylactic acid to the gelatins, any of known methods may be employed as far as it is possible to avoid severe reaction conditions which cause cut of molecular chains of the gelatin. Examples thereof may include a method of transforming the hydroxyl groups of the polylactic acid into a form capable of reacting an amino group, a carboxyl group or a hydroxyl group of the gelatin with a known method, and a method of condensing a hydroxyl group of the polylactic acid and a carboxyl group of the gelatin with a known method.

The derivatization reaction of the gelatin is carried out at a temperature of from 0 to 50° C., preferably 0 to 30° C. for 1 to 12 hours, preferably 2 to 6 hours.

The amount of the organic compound used in the derivatization reaction is from 0.1 to 50-fold mols, preferably 0.5 to 10-fold mols, more preferably 0.5 to 2-fold mols based on the functional groups (e.g., hydroxyl group, amino group or carboxyl group) to be reacted in the gelatin molecular chains. The derivatization reaction of the gelatin, namely, the grafting ratio of the organic compound to the gelatin can be controlled by regulating this weight ratio or changing the reaction temperature, reaction time, gelatin concentration, or the like.

The gelatin derivatives of the present invention are prepared by derivatizing all or a part of the gelatin functional groups to be derivatized with the organic compound. However, the derivatization percentage varies depending on the kind of the second component substances. The gelatin derivatives are selected from proper ones capable of causing the formation of the high-molecular weight micelle and proper ones capable of causing solubility of the second component substances such as hydrophobic drugs, etc.

The high-molecular weight micelle of the present invention can be prepared by, for example, dispersing the above gelatin derivatives with a critical micelle forming concentration (CMC) in water. Further, the high-molecular weight micelle of the present invention can be also prepared by dissolving the gelatin derivatives with CMC in an organic solvent and then dialyzing the resulting solution to water.

As the method of dispersing the gelatin in water, heat treatment, ultrasonic treatment, etc., are mentioned and these methods may be used singly or in combination. The heat treatment is carried out in the range of from 20 to 100° C. for 1 minute to 12 hours. The ultrasonic treatment is carried out in the range of 1 to 200 W for 1 second to 2 hours.

The CMC measurement can be carried out by an ordinary method as described in Examples described later.

The micelles of the present invention have various average particle diameters according to the gelatin used, the kind of the organic compounds for derivatization and the proportion of derivatization, for example, they have an average particle diameter of from 10 to 1000 nm, preferably 20 to 500 nm, more preferably 20 to 300 nm.

The particle diameter measurement can be carried out by an ordinary method using a dynamic light scattering device, etc., as described in Examples described later.

The high-molecular weight micelle complex of the present invention can be prepared by supporting the second components such as drugs, etc., on the above-mentioned high-molecular weight micelle.

Examples of the method of supporting the second components such as drugs, etc., may include a method of immersing the second component substance in lyophilized gelatin derivatives, thereafter preparing a micelle solution in the same manner as described above and thereby supporting the second component substance on the micelle, and a method of heat treating a gelatin derivative and a solution containing the second component substance followed by ultrasonic irradiation treatment in the same manner as described above.

Further, the high-molecular weight micelle complex comprised of the gelatin derivative and the second components can be prepared by lyophilizing a high-molecular weight micelle solution comprising the gelatin derivate, adding an aqueous solution of second components, and allowed to stand.

The pharmaceutical composition of the present invention can be prepared from the above-mentioned high-molecular weight micelle and may be optionally mixed with conventionally used excipients, additives etc.

The pharmaceutical composition of the present invention has excellent effect in the formation of sustained release of drugs, etc., life extension of drugs, etc., absorption of drugs, etc., from the skin or the mucous membrane tissue, targeting of drugs, etc., to target cells and solubilizing of drugs slightly soluble in water.

The anti-adhesive membranes of the present invention can be prepared from the above-mentioned gelatin derivatives, for example, by crosslinking the derivatives, and can be effectively used for preventing abdominal cavity, uterus serous membrane, etc., from adhesion after operation.

EXAMPLES

Hereinafter, the present invention is described in more detail with reference to the following Examples, but it should not be limited by the examples.

Example 1

Preparation of Gelatin Derivative Grafted with PEG

[Experimental Method]

Gelatin (manufactured by Nitta Gelatin Co., Ltd; derived from beef bones; molecular weight 100000; isoelectric point 5) was dissolved in dimethylsulfoxide (DMSO) so as to prepare a gelatin solution of a concentration of 10% (w/w). Further, methoxy polyethylene glycol succinimidyl succinate: SUNBRIGHT MEC-50HS (manufactured by NOF CORPORATION; molecular weight 5330) was dissolved in DMSO. The concentration of SUNBRIGHT MEC-50HS was two-fold mols of that of the amino group present in the gelatin. DMSO was previously dehydrated using molecular sieve 3A and submitted to use.

10 ml of the solution of SUNBRIGHT MEC-50HS was added little by little to 10 ml of the gelatin solution with stirring and reacted at room temperature for 3 hours. The synthetic scheme was shown in FIG. 1.

After the reaction, the reactant was dialyzed in ultra pure water using a cellulose tube (fractionation molecular weight 12000 to 14000). From starting the dialysis, the ultra pure water was changed after 1, 2, 4, 8, 12, 24, 36 and 48 hours, and thereby DMSO and unreacted SUNBRIGHT MEC-50HS, those obtainable by replacing succinimidyl succinate with carboxyl group, succinimidyl group eliminated substances were completely removed. The resulting compound (PEG-grafted gelatin) was lyophilized and kept at −20° C. until use.

Example 2

Evaluation on PEG-Grafted Gelatin

[Experimental Method]

With regard to the PEG-grafted gelatin prepared in Example 1, determination of amino group was carried out to evaluate the ratio of grafting SUNBRIGHT MEC-50HS to the gelatin.

The determination of amino group was carried out by the TNBS method. Namely, using an isotonic phosphate buffer with a pH of 7.4, 1 ml of a 4% (w/v) aqueous sodium hydrogen carbonate solution was added to 1 ml of the aqueous PEG-grafted gelatin solution having a concentration of 0.5 mg/ml. Further, 1 ml of 0.1% (w/v) sodium 2,4,6-trinitrobenzenesulfonate (TNBS) was added and subjected to reaction at 40° C. for 2 hours. After the reaction, the absorbance of a resulting yellow-colored aqueous solution was measured at a wavelength of 415 nm. Using β-alanine as a standard specimen, a calibration curve was made and the grafting ratio was determined from the calibration curve.

[Results]

With regard to the gelatin and the prepared PEG-grafted gelatin, the number of amino groups of each gelatin was determined by the TNBS method. In the gelatin before the PEG grafting, 28 amino residues were present per molecule. However, no amino group was detected in the PEG-grafted gelatin. From the facts, it was cleared that the SUNBRIGHT MEC-50HS was reacted with all the amino groups at the side-chain of various amino acids constituting the gelatin.

[Consideration]

The SUNBRIGHT MEC-50HS, which was a terminal active PEG could be grafted on the amino groups of the gelatin molecules. The amino groups remained in the PEG-grafted gelatin were determined by the TNBS method, and 28 mols of the SUNBRIGHT MEC-50HS was grafted on 1 mol of the gelatin having a molecular weight of 100000. As a result, it is considered that the molecular weight of the PEG-grafted gelatin was 250000.

Example 3

Preparation of PEG-Grafted Gelatin Micelle

[Experimental Method]

The PEG-grafted gelatin prepared in Example 1 was dissolved in an isotonic phosphate buffer with a pH of 7.4 so as to prepare a 10 mg/ml gelatin solution and then the resulting solution was subjected to ultrasonic treatment (10 μA) for 5 seconds using a probe type sonicator to prepare a transparent micelle solution.

Example 4

Measurement of Dynamic Light Scattering (DLS) of PEG-Grafted Gelatin Micelle

[Experimental Method]

With regard to 10 mg/ml of the PEG-grafted gelatin micelle prepared using an isotonic phosphate buffer with a pH of 7.4, the molecular size was measured by DLS-7000 (manufactured by Ootsuka Electronics Co., Ltd.). The measurement was carried out at scattering angles of 30°, 90° and 150° at 25° C.

[Results]

Figure 2:
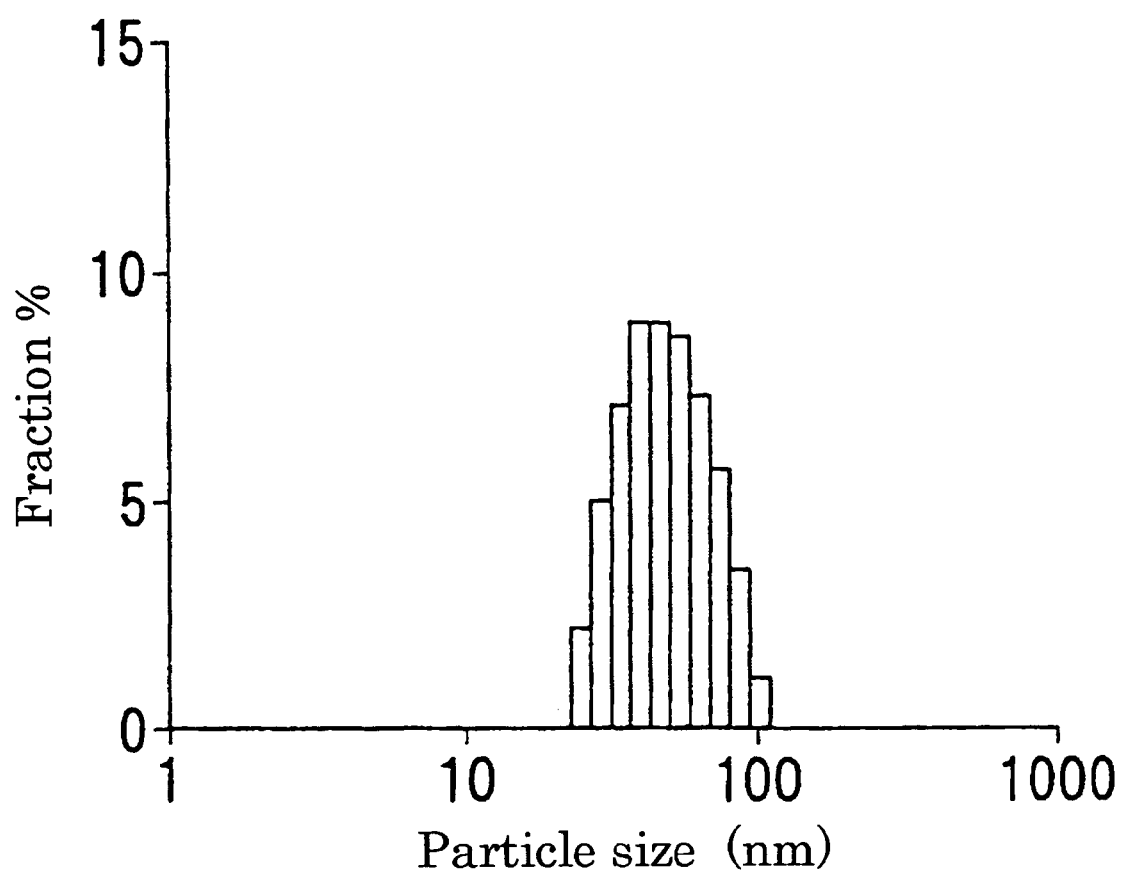
FIG. 2 is a diagram showing a particle size distribution of a PEG-grafted gelatin micelle.

The particle diameters of the PEG-grafted gelatin micelle were measured by DLS and the results were shown in FIG. 2.

The average particle diameter of the PEG-grafted gelatin micelle was 50 nm.

[Consideration]

As the method of micelle preparation from a solid specimen, a method of dissolving the solid specimen prepared by synthesis in water and a method of dissolving the solid specimen in an organic solvent and dialyzing the dissolved specimen against water have been used. The micelle of the present invention can be prepared by either of the above methods. From the viewpoint of operation convenience or preparation of the micelle having an accurate concentration, the former method is considered to be suitable. Therefore, in the present examples, the former method was employed. The PEG-grafted gelatin was dissolved in an isotonic phosphate buffer with a pH of 7.4 and the dissolved gelatin was subjected to ultrasonic treatment to prepare the micelle having a simply dispersed particle distribution.

Example 5

Measurement of Critical Micelle Formation Concentration (CMC)

[Experimental Method]

With regard to the PEG-grafted gelatin prepared, the critical micelle formation concentration (CMC) was measured. The CMC was measured by incorporating N-phenyl-1-naphtylamine (PNA) into the micelle. Using an isotonic phosphate buffer with a pH of 7.4, various concentrations—having PEG-grafted gelatin aqueous solutions were prepared. 0.1 ml of the PNA solution dissolved in methanol having a concentration of $5.0 \times 10^{-3}$M was added to 2 ml of the PEG-grafted gelatin solution and stirred for 2 minutes. Thereafter, the absorbance at a wavelength of 500 nm was measured using a spectrophotometer.

[Results]

Figure 3:
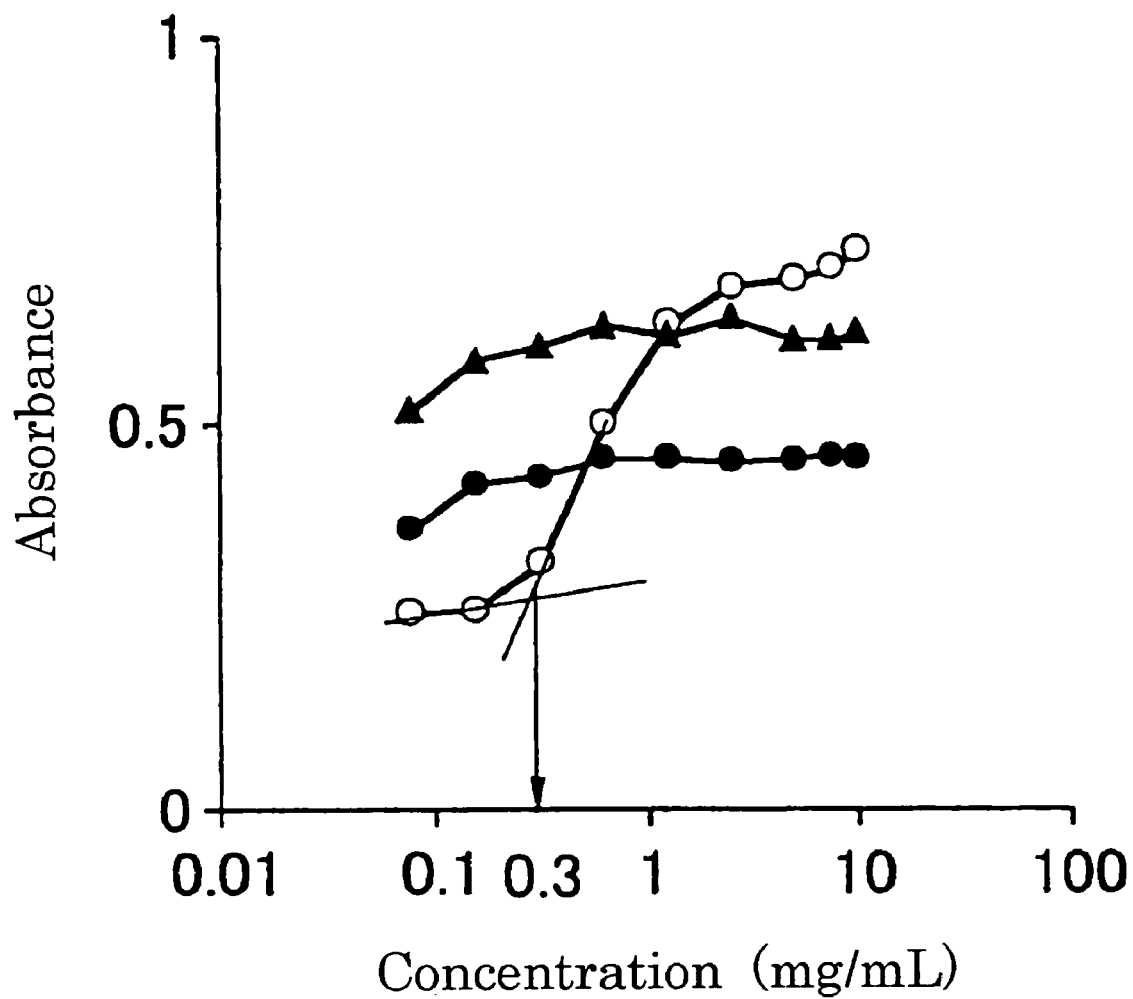
FIG. 3 is a diagram showing the results of CMC measurement of PEG-grafted gelatin. Sign ○ shows the PEG-grafted gelatin, sign ● shows the gelatin and sign ▲ shows SUN-BRIGHT MEC-50HS.

The incorporation of PNA into the PEG-grafted gelatin micelle was measured and the results were shown in FIG. 3.

The CMC of the PEG-grafted gelatin micelle was 0.3 mg/ml. In the gelatin alone or the SUNBRIGHT MEC-50HS alone, CMC was not admitted.

[Consideration]

As the CMC of the micelle used in this Example was a very small concentration of 0.3 mg/ml, it is considered that the stable micelle was formed in the blood even if in vivo intravenous administration wherein the micelle was administered into the body and then diluted rapidly. Further, different from conventional particles having a μm order, the average particle diameter of the micelle was 50 nm. Therefore, it is considered that it is possible to avoid RES or embolus after administration into the vein, to reach the micelle to the depth of the lung after endotracheal administration or to administer a dosage sufficient for curing by an extremely minute amount of the solution.

Example 6

Evaluation on Micelle Form by Affinity Column

[Experimental Method]

The forms of the core and the shell of micelle were studied using affinity column, which adsorbs gelatin. Namely, HiTrap (Trade Mark) Blue HP column (manufactured by Amersham Pharmacia Co., Ltd.) was washed with 10 ml of an isotonic phosphate buffer with a pH of 7.4 and thereafter, 0.5 ml of a PEG-grafted gelatin micelle solution was applied. 5 ml of the isotonic phosphate buffer with a pH of 7.4 was used as a bonding buffer and 5 ml of a 2M aqueous sodium chloride solution was used as an elution buffer. The solution was fractionated with each 0.4 ml portions and the gelatin in each of the fractions was measured by the Lowery method.

[Results]

Figure 4:
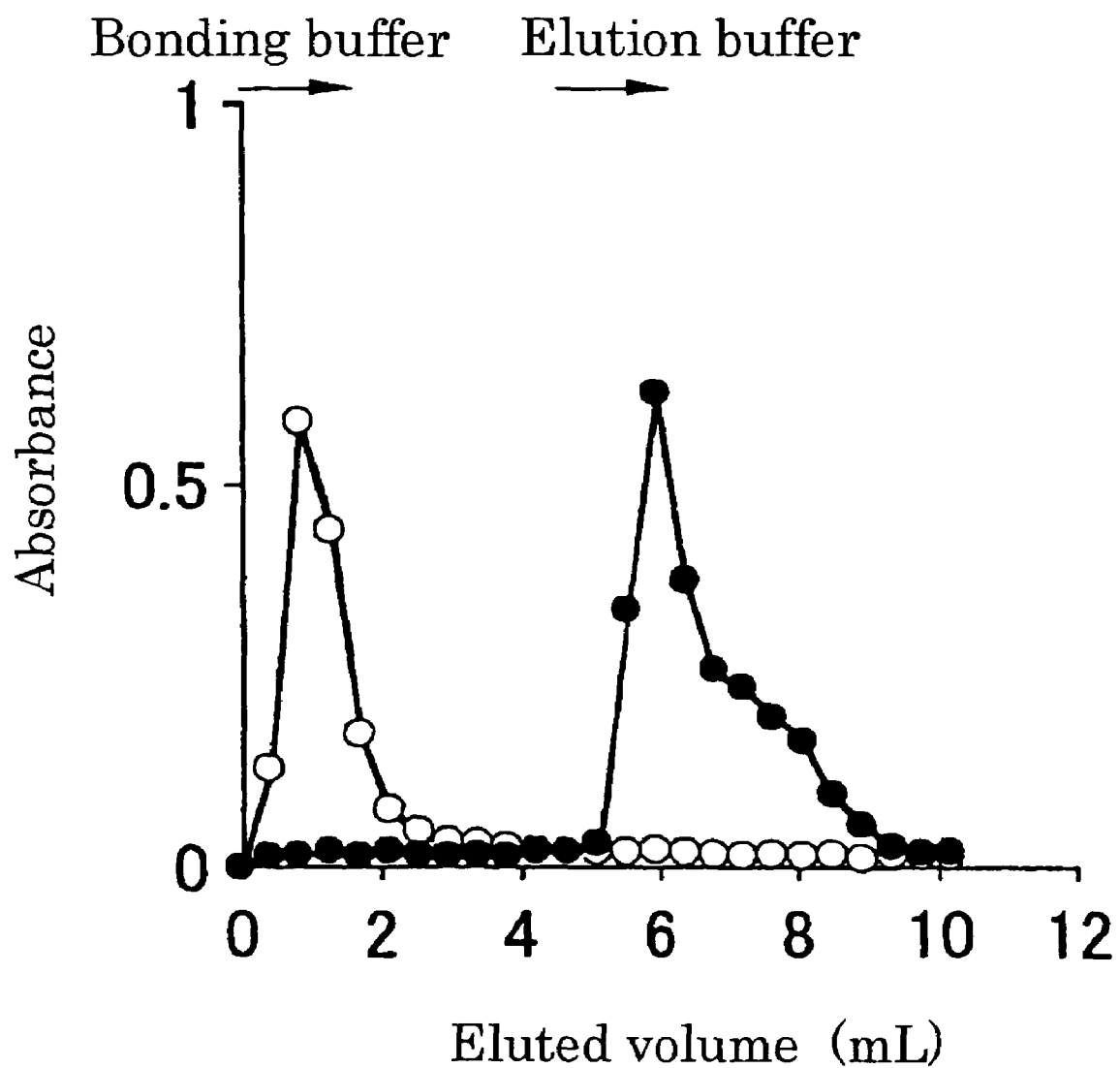
FIG. 4 is a diagram showing an elution profile of a PEG-grafted gelatin micelle solution from affinity column. Sign ○ shows the PEG-grafted gelatin micelle and ● shows the gelatin.

The PEG-grafted gelatin micelle solution was fractionated by HiTrap (Trade Mark) Blue HP column and the results were shown in FIG. 4.

In the case of applying the gelatin solution, the gelatin is adsorbed to the affinity column. In contrast, in the case of applying the PEG-grafted gelatin micelle solution, the PEG-grafted gelatin was eluted without adsorbing to the affinity column. From this fact, it was revealed that the gelatin was not present in the micelle surface.

[Consideration]

From the fractionation of the micelle by the affinity column, it is considered that the micelle in which the gelatin is present in the core and the PEG is present in the shell is formed.

Example 7

Measurement of CMC in Various Solutions

[Experimental Method]

With regard to gelatin molecular mutual interaction responsible for the formation of a micelle core, the electrostatic interaction and the hydrophobic interaction were studied. For investigating the electrostatic interaction, the CMC was measured using sodium chloride in phosphate buffers having various ion strengths (0.1, 0.2, 0.6 and 2) in the same manner as described above. Further, for investigating the hydrophobic interaction, the CMC was measured in a 6M guanidine hydrochloride aqueous solution.

[Results]

Figure 5:
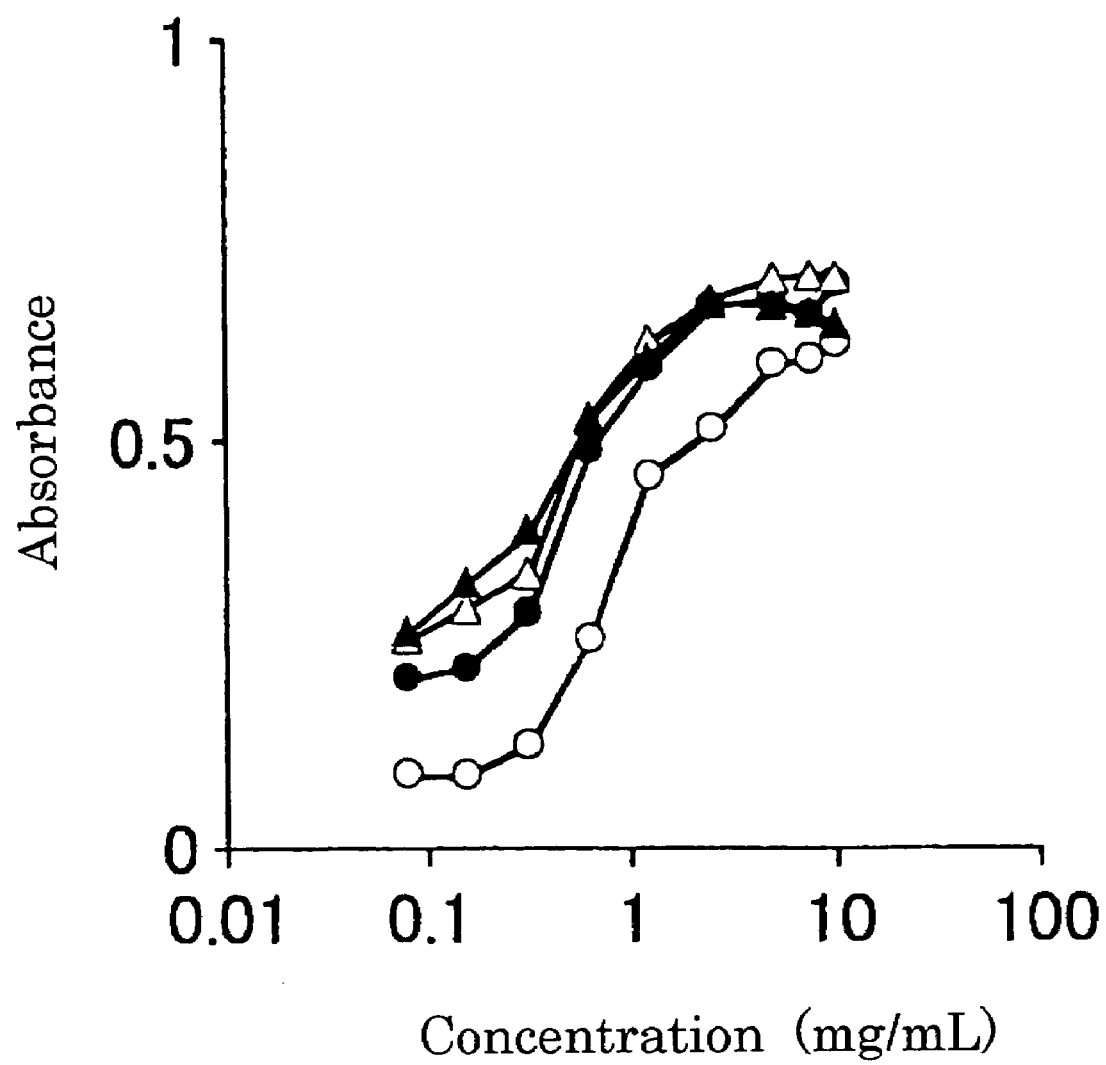
FIG. 5 is a diagram showing a measurement result of CMC of PEG-grafted gelatin in aqueous solutions having various ionic strengths. Sign ○ shows an ionic strength of 2, ● shows 0.6, Δ shows 0.2 and ▲ shows 0.1.
Figure 6:
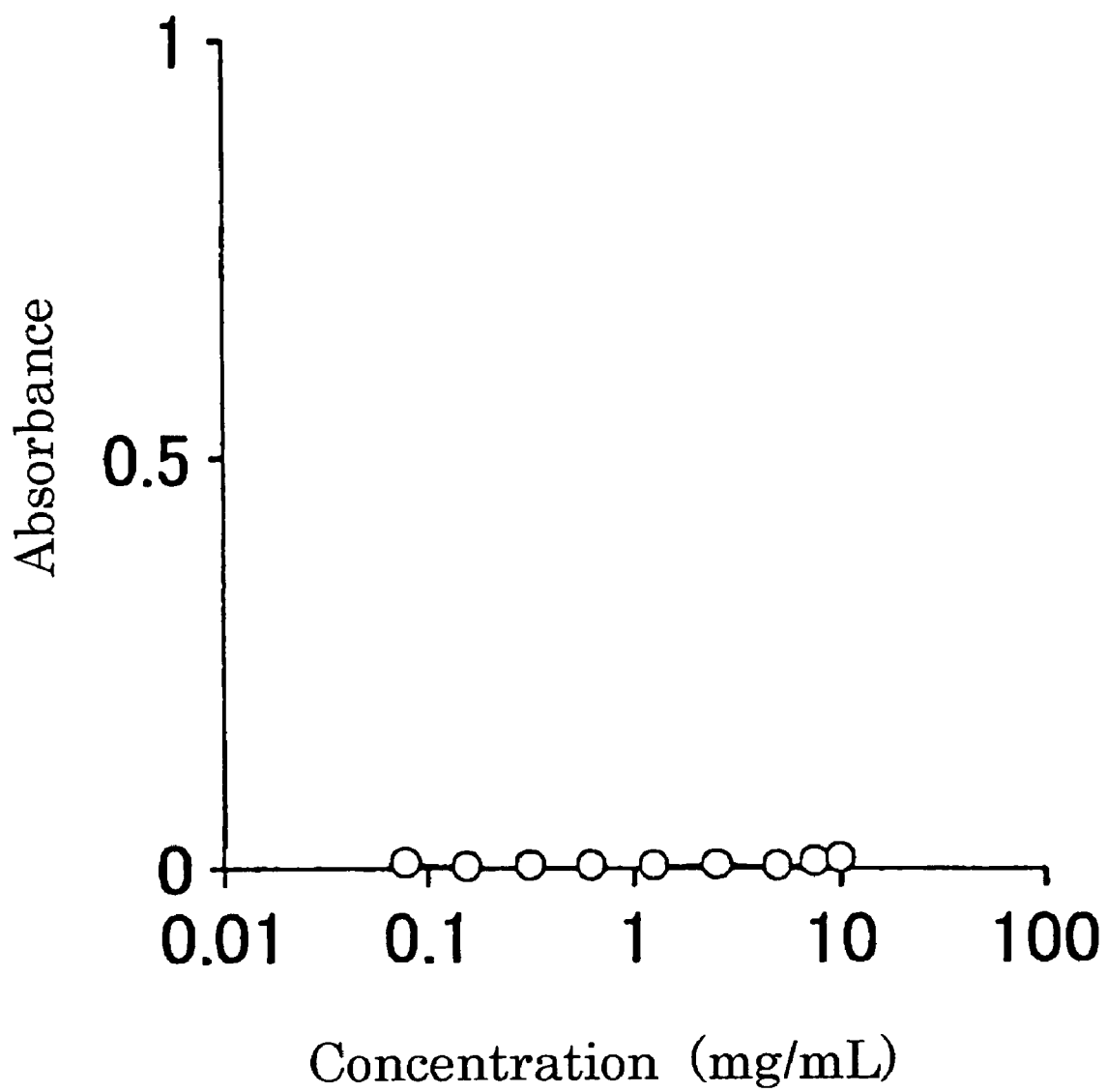
FIG. 6 is a diagram showing a measurement result of CMC in an aqueous solution of 6M guanidine hydrochloride.

Concerning to gelatin molecular mutual interaction responsible for the formation of a micelle core, the electrostatic interaction and the hydrophobic interaction were studied and the results were shown in FIG. 5 and FIG. 6.

As a result, the change was not found on the CMC of the PEG-grafted gelatin measured in the aqueous solutions having various ion strengths and the influence of ion strength to the CMC was not confirmed. In contrast, the CMC of the PEG-grafted gelatin was not measured in the 6M guanidine hydrochloride aqueous solution which is known to inhibit the hydrophobic interaction.

[Consideration]

It was revealed that among the gelatin molecular interactions, the electrostatic interaction did not affect the formation of the micelle core. In contrast, the CMC could not measured in the 6M guanidine hydrochloride aqueous solution and it is considered that the gelatin molecules are aggregated by the hydrophobic interaction rather than the electrostatic interaction, to form the micelle core.

Example 8

Incorporation of Peptide Drugs into PEG-Grafted Gelatin Micelle

[Experimental Method]

The incorporation of drugs into the PEG-grafted gelatin micelle prepared was studied. A basic fibroblast growth factor (bFGF) was used as a drug. Using a chloramine T, a $^{125}$I- labeled bFGF aqueous solution (0.02 ml) and an unlabeled bFGF aqueous solution (0.03 ml) were added to the PEG-grafted gelatin (5 mg) after the lyophilization prepared in Example 1 and were allowed to stand at 25° C. for 24 hours. Thereafter, they were dissolved in an isotonic phosphate buffer with a pH of 7.4 (0.5 ml) and thereby a micelle solution was prepared in the same manner as above. HiTrap (Trade Mark) Heparin HP column (manufactured by Amersham Pharmacia Co., Ltd.) which adsorbs bFGF was washed with 10 ml of an isotonic phosphate buffer with a pH of 7.4 and thereafter, 0.5 ml of a bFGF-containing micelle solution was applied. 5 ml of the isotonic phosphate buffer with a pH of 7.4 was used as a bonding buffer and 5 ml of a 2M aqueous sodium chloride solution was used as an elution buffer. The solution was fractionated with 0.4 ml portions and the bFGF contained in each micelle fraction was measured using a γ-counter, to determine an encapsulated ratio of the drug into the micelle.

[Results]
The encapsulated ratio of the bFGF into the PEG-grafted gelatin micelle was studied and it was found that 35% of the bFGF added was encapsulated in the micelle by mixing the bFGF and the PEG-grafted gelatin at 25° C. for 24 hours.

[Consideration]
The micelle prepared in this example has the gelatin in the core and the PEG in the shell. As the core was formed from the hydrophobic interaction of gelatin molecules, it is considered that the micelle core is further stably formed by the incorporation of a hydrophobic drug having a high protein bonding proportion into the micelle.

Further, the gelatin having an isoelectric point of 5 used in this Example is charged negatively in the pH 7.4 aqueous solution because the carboxyl group of the amino acid side chain is an ionic type. In the PEG-grafted gelatin, which was a reaction product, all of the amino groups, which are factors for charging positively, were made into PEG. On this account, it is considered that the micelle core was negatively charged by the carboxyl group of the gelatin. Therefore, it is further considered that the stability of the micelle core is also increased by a polyion complex formed from the bFGF having a positive charge in pH 7.4 and the negative charge of the micelle core. As is clear from the results, the bFGF could be encapsulated in the micelle at 25° C. Further, the stability of the core is increased by the incorporation of the drug into the micelle core and the formation of sustained release of the encapsulated drug can be attained. On this account, it is considered to apply the micelle as a DDS agent.

Example 9

Preparation of Succinated Gelatin

[Experimental Method]
The gelatin as described in Example 1 was dissolved in DMSO so as to prepare a 12.5 wt % (w/w) gelatin solution. A succinic anhydride (available from NACALAI TESQUE) was dissolved in DMSO to prepare solutions having various concentrations. Each solution was mixed with the gelatin dissolved DMSO and reacted at 37° C. for 1 hour. After completion of the reaction, the reaction product was re-precipitated in a large excess of acetone and the precipitate was washed with acetone three times. Each of the resulting samples was dried in vacuo to prepare succinated gelatin. The amino group of the succinated gelatin was determined by the TNBS method.

[Results]
The amino groups of the gelatin and the succinated gelatin were determined by the TNBS method and it was found that when 0.132, 0.266 or 0.542 mmol of the succinic anhydride was added, 6.6%, 28.3% or 83.5% of the amino groups of the gelatin used in the reaction was converted into carboxyl groups, respectively. As 28 mols of amino group is present in one molecule of the gelatin, it was revealed that when 0.132, 0.266 or 0.542 mmol of the succinic anhydride was added, 26 mols, 20 mols or 5 mols of amino group was present in one molecule of the succinated gelatin, respectively.

Example 10

Preparation of PEG-Grafted Succinated Gelatin Derivatives

[Experimental Method]
The succinated gelatin prepared in Example 9 was dissolved in DMSO so as to prepare a succinated gelatin solution of a concentration of 10% (w/w). Further, SUNBRIGHT MEC-50HS was dissolved in DMSO. The concentration of the SUNBRIGHT MEC-50HS was set to be 2-fold mols of that of the amino group present in the succinated gelatin. 10 ml of the SUNBRIGHT MEC-50HS solution was added little by little to 10 ml of the gelatin solution with stirring and reacted at room temperature for 3 hours. After the reaction, the reactant was dialyzed against ultra pure water using cellulose tube (fractionation molecular weight 12000-14000). From starting the dialysis, the ultra pure water was changed after 1, 2, 4, 8, 12, 24, 36 and 48 hours, and thereby DMSO and unreacted SUNBRIGHT MEC-50HS were completely removed. The resulting compound (PEG-grafted succinated gelatin) was lyophilized and kept at −20° C. until use.

Example 11

Evaluation of PEG-Grafted Succinated Gelatin Derivative

[Experimental Method]
With regard to the PEG-grafted succinated gelatin derivatives prepared, determination of amino group was carried out to evaluate the percentage of grafting SUNBRIGHT MEC-50HS to the gelatin. The determination of amino group was carried out by the TNBS method.

As a result, amino group was not detected in the PEG-grafted succinated gelatin derivatives. From the fact, it was revealed that the SUNBRIGHT MEC-50HS was reacted with all of the amino groups at the side chains of the succinated gelatin.

[Consideration]
The SUNBRIGHT MEC-50HS was reacted with all of the amino groups in the succinated gelatin side chains. When 0.132, 0.266 or 0.542 mmol of the succinic anhydride was added, the SUNBRIGHT MEC-50HS in one molecule of the PEG-grafted succinated gelatin derivative was 26 mols, 20 mols or 5 mols, respectively. As a result, it is considered that the molecular weight of the PEG-grafted succinated gelatin derivative was 240000, 200000 or 130000, respectively.

Example 12

Preparation of PEG-Grafted Succinated Gelatin Micelle

The PEG-grafted succinated gelatin derivative thus prepared was dissolved in an isotonic phosphate buffer with a pH of 7.4 so as to prepare a 10 mg/ml derivative solution and then the solution was subjected to ultrasonic treatment (10 μA) for 5 seconds using a probe type sonicator to prepare a transparent micelle solution.

Example 13

Measurement of Critical Micelle Formation Concentration (CMC) of PEG-Grafted Succinated Gelatin

[Experimental Method]

With regard to the PEG-grafted succinated gelatin prepared, the critical micelle forming concentration (CMC) was measured. The CMC was measured by incorporating N-phenyl-1-naphtyl amine (PNA) into the micelle. Using an isotonic phosphate buffer with a pH of 7.4, PEG-grafted succinated gelatin aqueous solutions with various concentrations were prepared. 0.1 ml of the PNA methanol solution having a concentration of $5.0 \times 10^{-3}$ M was added to 2 ml of the PEG-grafted succinated gelatin solution and stirred for 2 minutes. Thereafter, the absorbance at a wavelength of 500 nm was measured using a spectrophotometer.

[Results]

Figure 7:
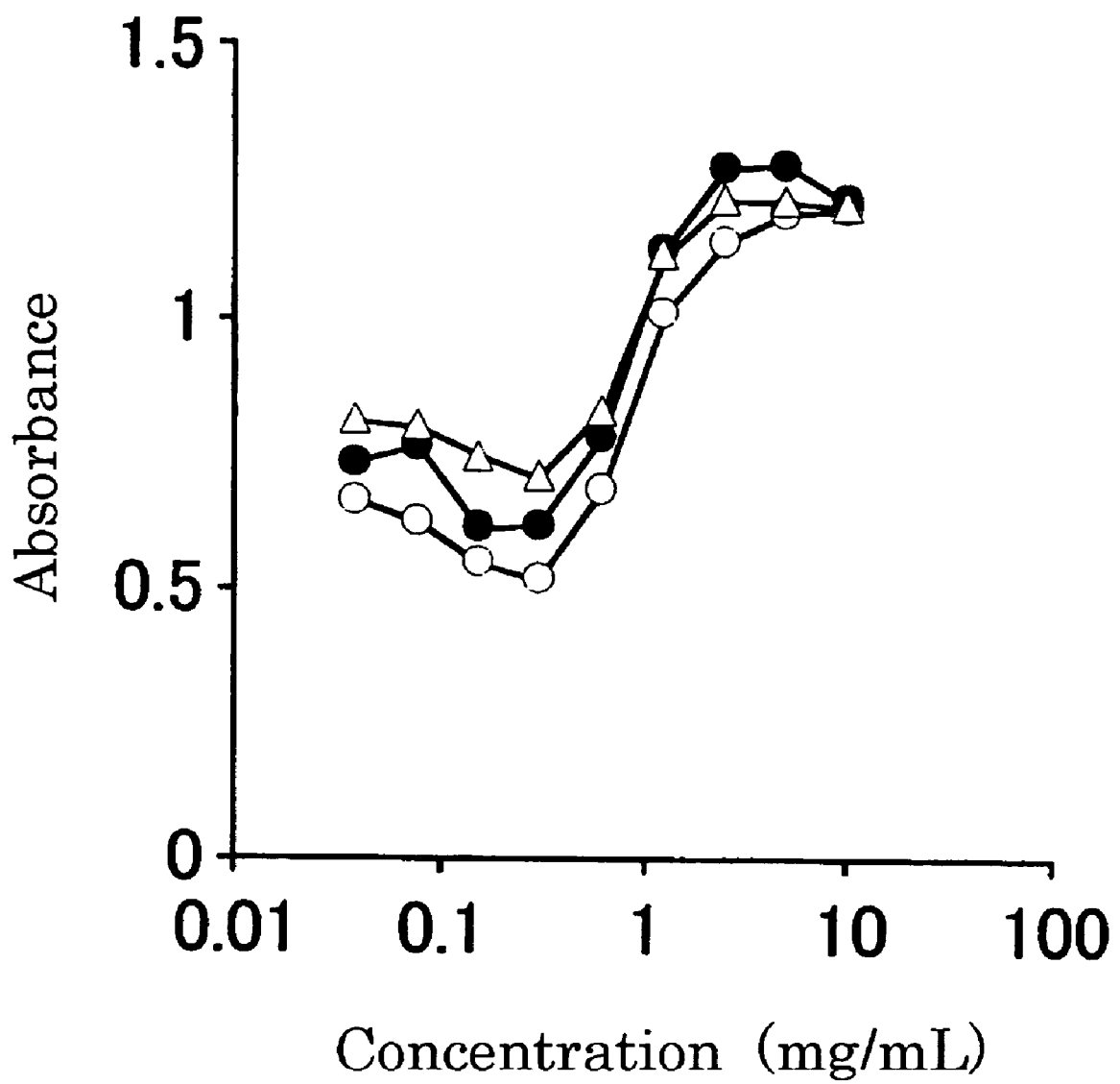
FIG. 7 is a diagram showing a measurement result of CMC of PEG-grafted succinated gelatin. Sign ○ shows a succination percentage of 6.6%, ● shows 28.3% and Δ shows 83.5%.

The incorporation of PNA into the PEG-grafted succinated gelatin micelle was measured and the results were shown in FIG. 7.

The CMC of the PEG-grafted succinated gelatin micelle was 0.3 mg/ml irrespective of the succination rate.

Example 14

Evaluation on Micelle Form of PEG-Grafted Succinated Gelatin Micelle by Affinity Column

[Experimental Method]

The forms of the core and the shell of the micelle was studied using affinity column in which gelatin was adsorbed. Namely, HiTrap (Trade Mark) Blue HP column (manufactured by Amersham Pharmacia Co., Ltd.) was washed with 10 ml of an isotonic phosphate buffer with a pH of 7.4 and thereafter, 0.5 ml of a PEG-grafted gelatin micelle solution was applied. 5 ml of the pH isotonic phosphate buffer with a pH of 7.4 was used as a bonding buffer and 5 ml of a 2M aqueous sodium chloride solution was used as an elution buffer. The solution was fractionated with each 0.4 ml portions and the gelatin in each fraction was measured by the Lowery method.

[Results]

Figure 8:
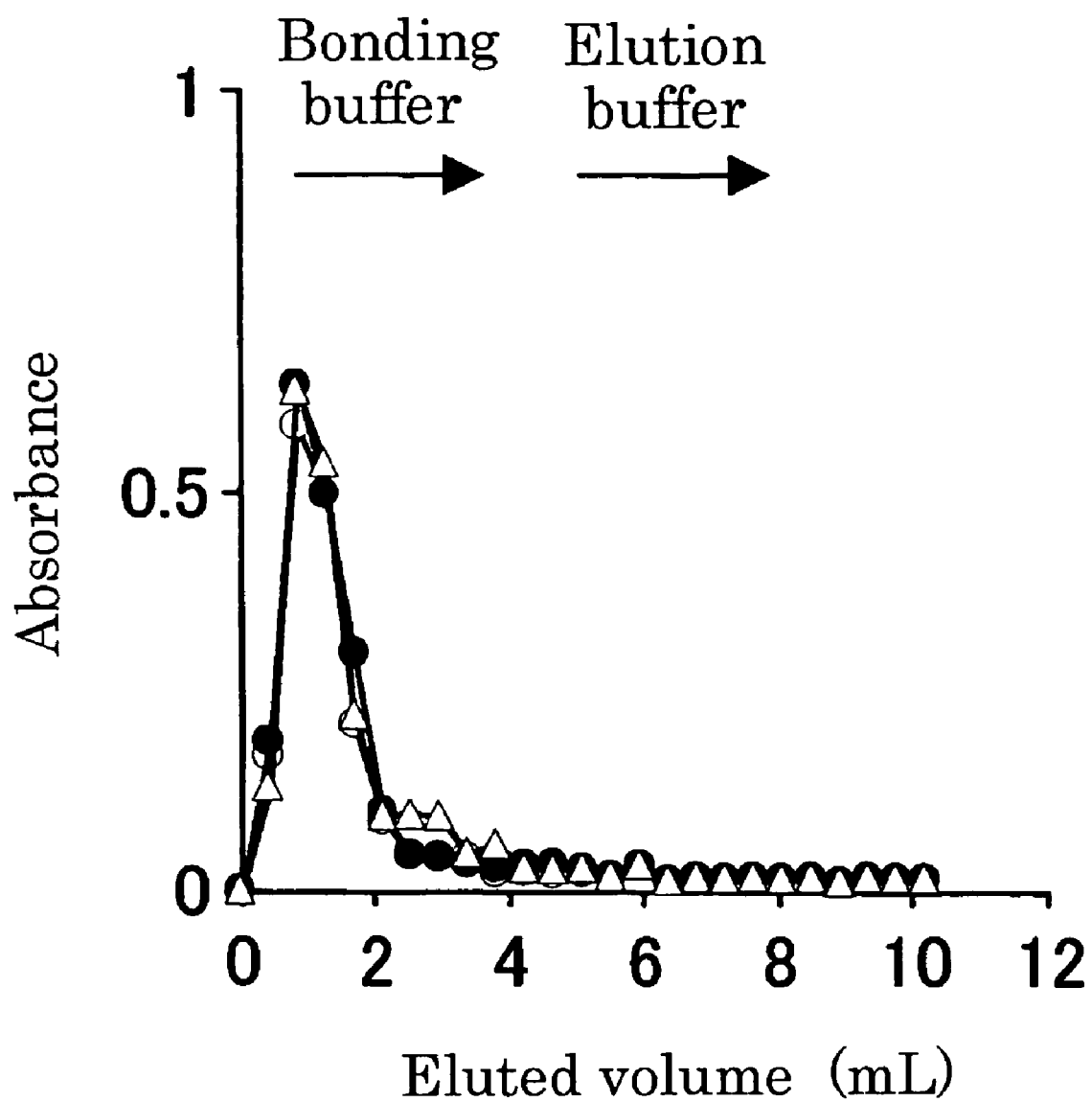
FIG. 8 is a diagram showing an elution profile of a PEG-grafted succinated gelatin micelle solution from affinity column. Sign ○ shows a succination percentage of 6.6%, ● shows 28.3% and Δ shows 83.5%.

The PEG-grafted succinated gelatin micelle solution was fractionated by HiTrap (Trade Mark) Blue HP column and the results were shown in FIG. 8.

In the case of applying the PEG-grafted succinated gelatin solution, in the PEG-grafted succinated gelatin micelle solution having any of the succination rate, the micelle was eluted without adsorbing to the affinity column. From this fact, it was revealed that the gelatin was not present in the micelle surface.

[Consideration]

From the fractionation of the micelle by the affinity column, it is considered that the micelle in which the succinated gelatin is present in the core and the PEG is present in the shell is formed.

Example 15

Incorporation of Peptide Drugs into PEG-Grafted Succinated Gelatin Micelle

[Experimental Method]

The incorporation of drugs into the PEG-grafted succinated gelatin micelle prepared was studied. A basic fibroblast growth factor (bFGF) was used as a drug. Using a chloramine T, a $^{125}$I-labeled bFGF aqueous solution (0.02 ml) and an unlabeled bFGF aqueous solution (0.03 ml) were added to the PEG-grafted succinated gelatin (5 mg) after the lyophilization prepared in Example 10 and were allowed to stand at 25° C. for 24 hours. Thereafter, they were dissolved in an isotonic phosphate buffer with a pH of 7.4 (0.5 ml) and thereby a micelle solution was prepared in the same manner as mentioned above. HiTrap (Trade Mark) Heparin HP column (manufactured by Amersham Pharmacia Co., Ltd.) which adsorbs bFGF was washed with 10 ml of an isotonic phosphate buffer with a pH of 7.4 and thereafter, 0.5 ml of a bFGF-containing micelle solution was applied. 5 ml of the isotonic phosphate buffer with a pH of 7.4 was used as a bonding buffer and 5 ml of a 2M aqueous sodium chloride solution was used as an elution buffer. The solution was fractionated with each 0.4 ml portions and the bFGF contained in each micelle fraction was measured using a γ-counter, to determine an encapsulated ratio of the drug into the micelle.

[Results]

The encapsulated ratio of the bFGF into the PEG-grafted succinated gelatin micelle was studied and it was found that in the PEG-grafted succinated gelatin having a succination rate of 6.6%, 28.3% or 83.5% prepared by mixing the bFGF and the PEG-grafted gelatin at 25° C. for 24 hours, 42.3%, 40.0% or 28.0% of the bFGF was encapsulated in the micelle, respectively.

[Consideration]

In the micelle having the succinated gelatin in the micelle core, the bFGF could be encapsulated. Further, the succinated gelatin was charged negatively in the pH isotonic phosphate buffer with a pH of 7.4, while the bFGF was positively charged. On this account, it is considered that the bFGF was encapsulated into the micelle core by electrostatic interaction. Further, the gelatin was succinated and thereby the negative charge of the core could be increased as compared with the gelatin without succination. Therefore, it is considered that the encapsulated ratio of the bFGF having positive charge was increased.

Example 16

Sustained Release Experiment of bFGF from PEG-Grafted Succinated Gelatin Micelle

[Experiment Method]

A $^{125}$I-labeled bFGF aqueous solution (0.02 ml) using a chloramine T, an unlabeled bFGF aqueous solution (0.03 ml) and an isotonic phosphate buffer with a pH of 7.4 (0.025 ml) were added to the PEG-grafted succinated gelatin (5 mg) after the lyophilization prepared in Example 10 and were allowed to stand at 25° C. for 24 hours. Thereafter, they were dissolved in an isotonic phosphate buffer with a pH of 7.4 (0.5 ml) and thereby a micelle solution was prepared in the same manner as mentioned above. HiTrap (Trade Mark) Heparin HP column (manufactured by Amersham Pharmacia Co., Ltd.) which adsorbs bFGF was washed with 10 ml of an isotonic phosphate buffer with a pH of 7.4 and thereafter, 0.5 ml of a bFGF-containing micelle solution was applied. 5 ml of the pH isotonic phosphate buffer with a pH of 7.4 was used as a bonding buffer to remove bFGF which had not been encapsulated, and thereby only a micelle fraction was obtained. This micelle solution was incubated in an aqueous solution at 37° C. After 0.5, 1, 3 and 6 hours, the micelle solution was fractionated using HiTrap (Trade Mark) Heparin HP column in the same manner as mentioned above, and thereby the decreased amount of the bFGF encapsulated in the micelle was measured.

[Results]

Figure 9:
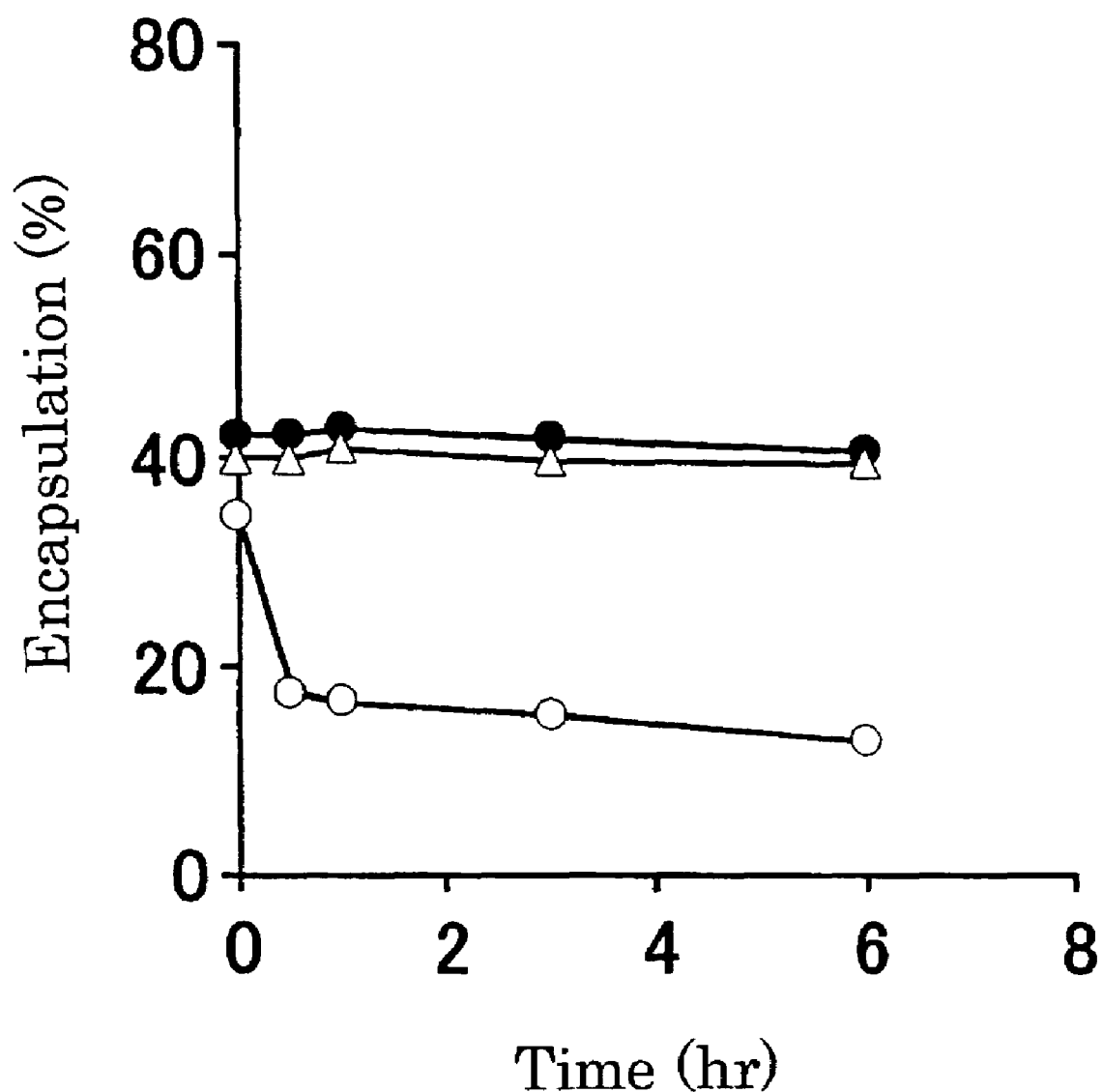
FIG. 9 is a diagram showing a sustained release result of bFGF from a PEG-grafted succinated gelatin micelle. Sign ○ shows a succination percentage of 0%, ● shows 6.6% and Δ shows 28.3%.

The decreased amount of the bFGF in the PEG-grafted succinated gelatin at 37° C. was measured and the results were shown in FIG. 9. From the PEG-grafted gelatin micelle prepared by using the unsuccinated gelatin, the bFGF was released quickly, while in the PEG-grafted succinated gelatin micelle prepared by using the succinated gelatin, the encapsulated bFGF was not released.

[Consideration]

In the micelle prepared by using the PEG-grafted succinated gelatin, the encapsulated bFGF was not released. From the fact, it is considered that the bFGF having negative charge and positive charge of the micelle core prepared by using the PEG-grafted succinated gelatin shows electrostatic interaction and the bFGF stays in the micelle core. Therefore, it is further considered that the bFGF encapsulated PEG-grafted succinated gelatin micelle is administrated in vivo and thereafter the micelle is disintegrated by gelatin decomposition caused by enzymes, etc., and thereby the bFGF is released.

Example 17

Preparation of Cationized Gelatin

[Experimental Method]

10 g of gelatin (manufactured by Nitta Gelatin Inc.; derived from pig skin; molecular weight 100000; isoelectric point 9) was dissolved in 0.1 M phosphate buffer to prepare a 4% (w/w) solution. To the solution, 27.9 g of ethylene-diamine was mixed and then the pH thereof was regulated to 5.0 by hydrochloric acid. Further, 5.3 g of 1-ethyl-3-(3-dimethylaminopropyl)-carbodiimide was added to the solution to make up to 500 mL using a phosphate buffer. The mixed solution was allowed to react at 37° C. for 18 hours, and thereafter, the reactant was dialyzed against ultra pure water using a cellulose tube (fractionation molecular weight 12000 to 14000). From starting the dialysis, the ultra pure water was changed after 1, 2, 4, 8, 12, 24, 36 and 48 hours, and thereby unreacted ethylenediamine and 1-ethyl-3-(3-dimethylaminopropyl)-carbodiimide were removed. The resulting sample was lyophilized to prepare cationized gelatin. The amino group of the cationized gelatin was determined by the TNBS method and thereby the cationization degree of the gelatin was determined.

[Results]

The amino groups of the gelatin and the cationized gelatin were determined by the TNBS method and it was found that 47% of carboxyl groups of the gelatin used in the reaction was converted into amino groups.

Example 18

Preparation of PEG-Grafted Cationized Gelatin Derivative

[Experimental Method]

The cationized gelatin prepared above was dissolved in DMSO so as to prepare a gelatin solution having a concentration of 10% (w/w). SUNBRIGHT MEC-50HS was dissolved in DMSO.

The concentration of SUNBRIGHT MEC-50HS was set to be 0.5-fold mols that of the amino group present in the cationized gelatin.

Further, 10 ml of the SUNBRIGHT MEC-50HS solution was added little by little to 10 ml of the gelatin solution with stirring and allowed to react at room temperature for 3 hours. After the reaction, the reactant was dialyzed against ultra pure water using a cellulose tube (fractionation molecular weight 12000 to 14000). From starting the dialysis, the ultra pure water was changed after 1, 2, 4, 8, 12, 24, 36 and 48 hours, and thereby DMSO and unreacted SUNBRIGHT MEC-50HS were completely removed. The resulting compound (PEG-grafted cationized gelatin) was lyophilized and kept at −20° C. until use.

Example 19

Evaluation of PEG-Grafted Cationized Gelatin Derivative

[Experimental Method]

With regard to the PEG-grafted cationized gelatin prepared, determination of amino group was carried out to evaluate the percentage of grafting SUNBRIGHT MEC-50HS to the gelatin. The determination of amino group was carried out by the TNBS method.

[Results]

The amino group number of the PEG-grafted cationized gelatin was measured by the TNBS method and it was revealed that SUNBRIGHT MEC-50HS was reacted with 50.9% of amino groups in the cationized gelatin used for the reaction.

Example 20

Interaction (1) of PEG-Grafted Cationized Gelatin with Plasmid DNA

[Experimental Method]

For using the PEG-grafted cationized gelatin prepared as a DNA carrier in a drug delivery system (DDS), the interaction of the PRG grafted cationized gelatin with the plasmid DNA was studied. pSV-lacZ was used as a model plasmid DNA. Solutions were prepared in a weight ratio of the PEG-grafted cationized gelatin to the plasmid DNA of 0.25, 0.5, 1, 2.5, 5, 10 and 50, respectively. Each of the solutions was subjected to electrophoresis using a 0.8% agarose gel. The agarose gel was previously soaked with ethidium bromide.

[Results]

Figure 10:
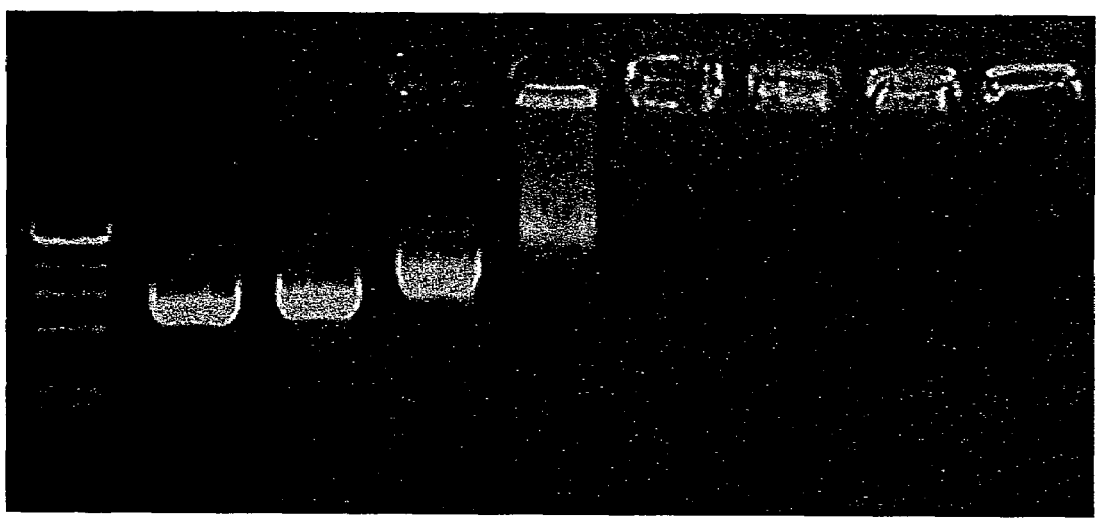
FIG. 10 is a photograph showing a result of electrophoresis of PEG-grafted cationized gelatin/plasmid DNA. Lane 1: molecular weight maker; Lane 2: free plasmid DNA; Lanes 3 to 9: gelatin derivatives/plasmid DNA having a weight ratio of 0.25, 0.5, 1, 2.5, 5, 10 and 50.

The results of carrying out the electrophoresis are shown in FIG. 10.

[Consideration]

From the results of the electrophoresis, it is considered that when the weight ratio of the PEG-grafted cationized gelatin to the plasmid DNA is 2.5 or more, the electrophoresis of the plasmid DNA was not performed because the plasmid DNA formed a complex together with the PEG-grafted cationized gelatin.

From the fact, it was further considered that the complex of the PEG-grafted cationized gelatin prepared and the plasmid DNA can be used as a DNA carrier in DDS.

Example 21

Interaction (2) of PEG-Grafted Cationized Gelatin with Plasmid DNA

[Experimental Method]

Each of the solutions prepared in a weight ratio of the PEG-grafted cationized gelatin to the plasmid DNA of 0.25, 0.5, 1, 2.5, 5, 10 and 50, respectively, was studied using HiTrap™ Heparin HP column (manufactured by Amersham Pharmacia Co., Ltd.) known to adsorbs gelatin.

Namely, HiTrap™ Blue HP column (manufactured by Amersham Pharmacia Co., Ltd.) was washed with 10 ml of an isotonic phosphate buffer with a pH of 7.4 and thereafter, 0.5 ml of the PEG-grafted cationized gelatin/$^{125}$I-plasmid DNA solution was applied. 5 ml of the pH isotonic phosphate buffer with a pH of 7.4 was used as a bonding buffer and 5 ml of a 2M aqueous sodium chloride solution was used as an elution buffer. The solution was fractionated with each 0.4 ml portions and the amount of the plasmid DNA in each fraction was measured by a γ-counter. From the measurement, it is considered that the plasmid DNA eluted with the bonding buffer was not interacted with the PEG-grafted cationized gelatin. The proportion of forming the complex of the plasmid DNA and the PEG-grafted cationized gelatin in each of the mixing weight ratios was determined.

[Results]

Figure 11:
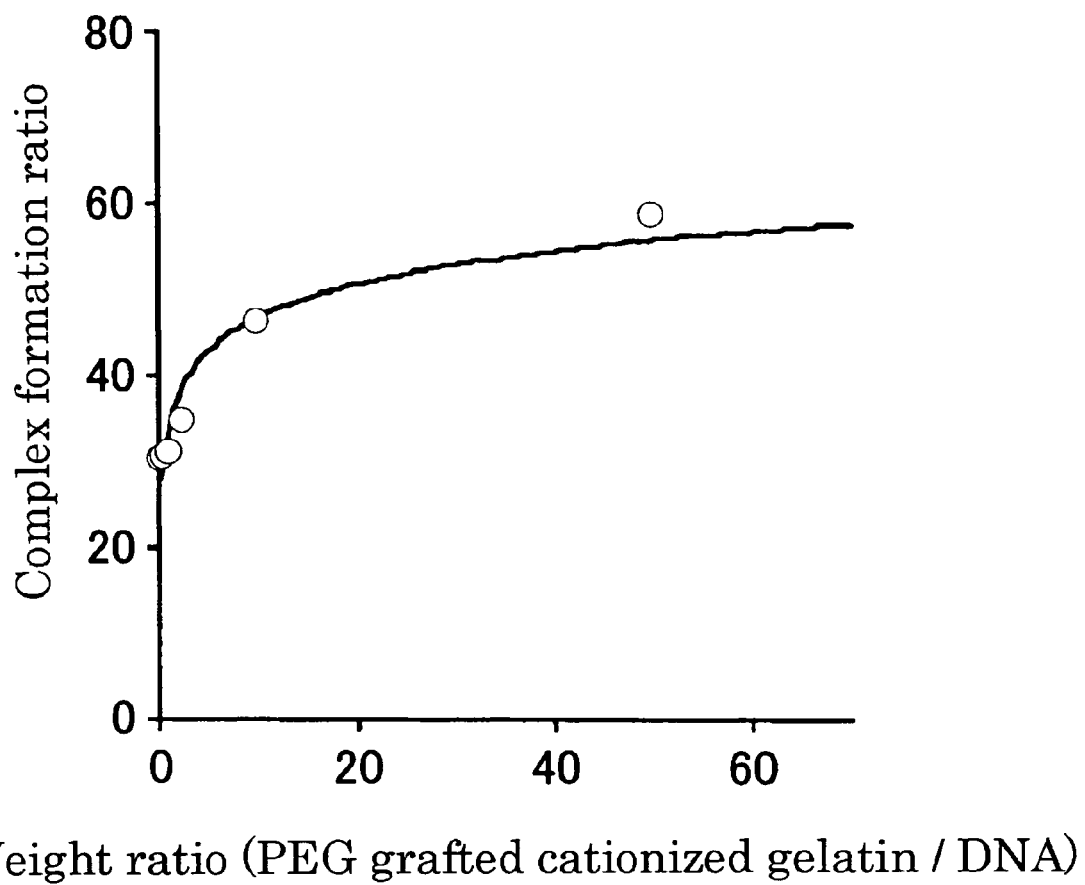
FIG. 11 is a diagram showing a complex forming ratio of PEG-grafted cationized gelatin/plasmid DNA.

The results using the column are shown in FIG. 11.

[Consideration]

In any one of the mixing ratios, the PEG-grafted cationized gelatin forms the complex together with the plasmid DNA and it is revealed that the complex forming rate is increased together with the mixing weight ratio thereof. Furthermore, the plasmid DNA itself was not adsorbed to the column in accordance with our expectations.

From the fact, it is found that the PEG-grafted cationized gelatin prepared and the plasmid DNA form the complex.

Example 22

Preparation of Gelatin Derivatives Grafted in Different Grafting Ratio by PEG's Having Various Molecular Weights

[Experimental Method]

Using methoxy polyethylene glycol succinimidyl succinates having various molecular weights in different amounts, grafted gelatin derivatives were prepared in different grafting percentages by the method as described in Example 1.

The PEG portions of the methoxy polyethylene glycol succinimidyl succinates used each had a molecular weight of 2000, 5000 and 12000, respectively.

Each of the methoxy polyethylene glycol succinimidyl succinates was used in an amount of from 0.05 to 2-fold mols based on the amino groups present in the gelatin.

The grafting percentages of the resulting gelatin derivatives were measured in the same manner as in Example 2.

[Results]

Figure 12:
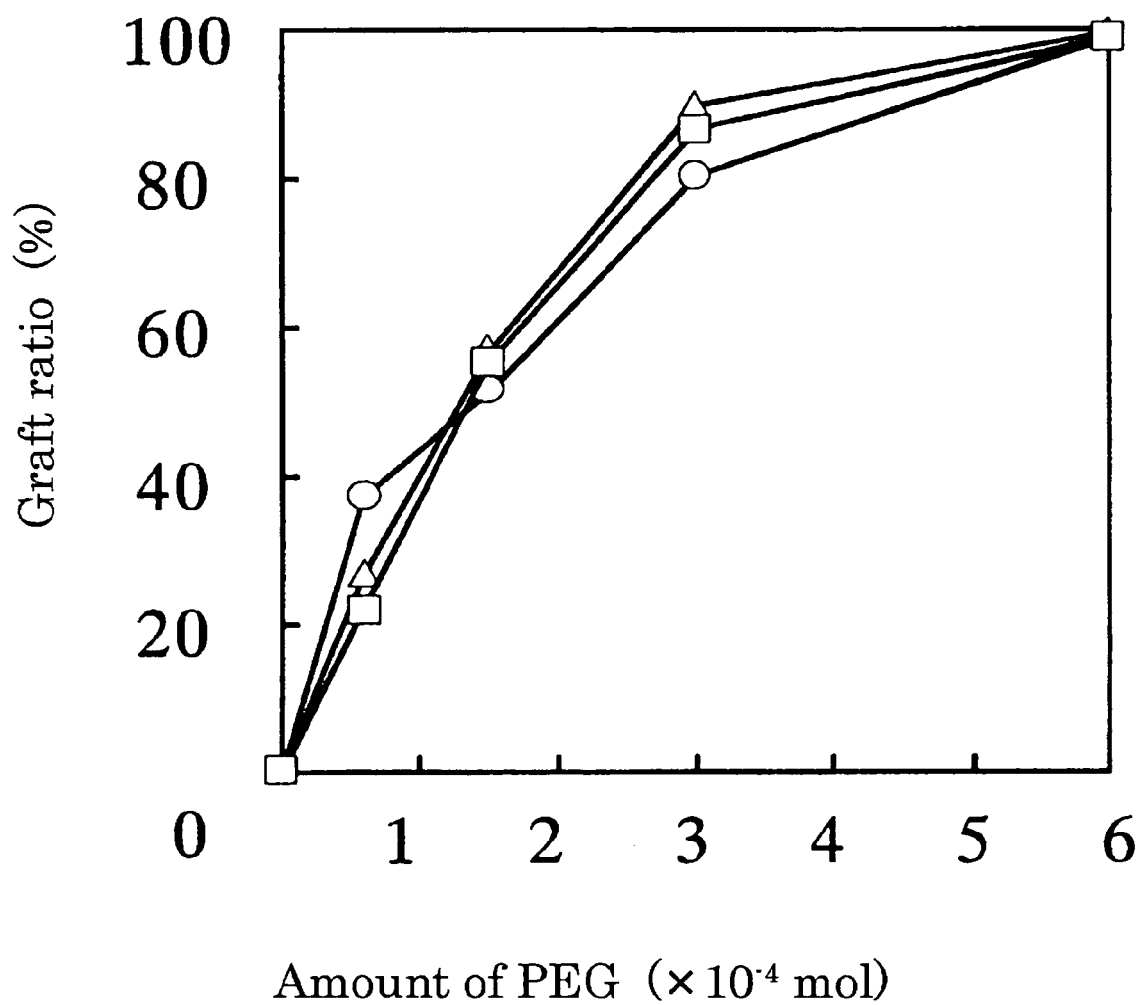
FIG. 12 is a diagram showing a relation of an amount of a PEG derivative used and a grafting ratio of PEG-grafted gelatin. Sign ○ shows a PEG portion having a molecular weight of 2000, Δ shows a PEG portion having a molecular weight of 5000 and □ shows a PEG portion having a molecular weight of 12000.

The grafting percentages in the gelatin derivatives were shown in FIG. 12. Based on the amino groups present in the gelatin, the grafting ratio was about 20 to 40% in the case of using 0.1-fold mol of the PEG derivative, it was about 50 to 55% in the case of using 0.5-fold mol of the PEG derivative, it was about 80 to 85% in the case of using 1-fold mol of the PEG derivative and it was almost 100% in the case of using 2-fold mols of the PEG derivative.

Example 23

Measurement of CMC in Various PEG-Grafted Gelatin Derivatives

[Experimental Method]

Micelle solutions were prepared in accordance with the method of Example 3 from the PEG-grafted gelatin derivatives prepared in Example 22 and the CMC of each derivative was measured in accordance with Example 5.

[Results]

Figure 13:
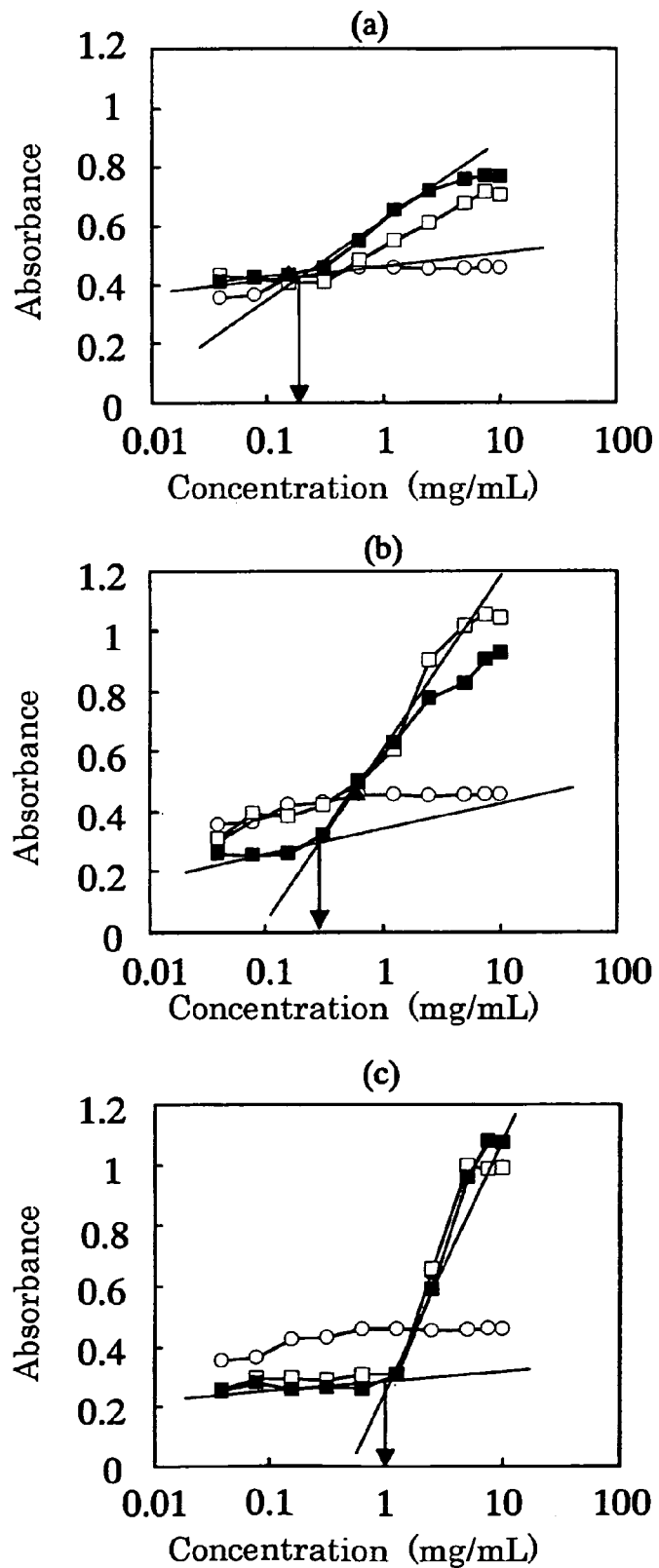
FIG. 13 is a diagram showing a measurement result of CMC of PEG-grafted gelatin. (a), (b) and (c) show the cases of PEG portions having a molecular weight of 2000, 5000 and 12000, respectively. Sign ○ shows a grafting ratio of 0%, □ shows 85% and ■ shows 100%.

The CMC of each of the PEG-grafted gelatin derivative was shown in FIG. 13. In the gelatin derivative grafted with the PEG having a molecular weight of 2000, the CMC was about 0.2 mg/ml, in the gelatin derivative grafted with the PEG having a molecular weight of 5000, the CMC was about 0.3 mg/ml and in the gelatin derivative grafted with the PEG having a molecular weight of 12000, the CMC was about 1 mg/ml.

Example 24

Affinity Chromatography of Various Kinds of PEG-Grafted Gelatin Derivatives

[Experimental Method]

Each of the PEG-grafted gelatin derivatives prepared in Example 22 was studied using affinity column in the same manner as in Example 6.

[Results]

Figure 14:
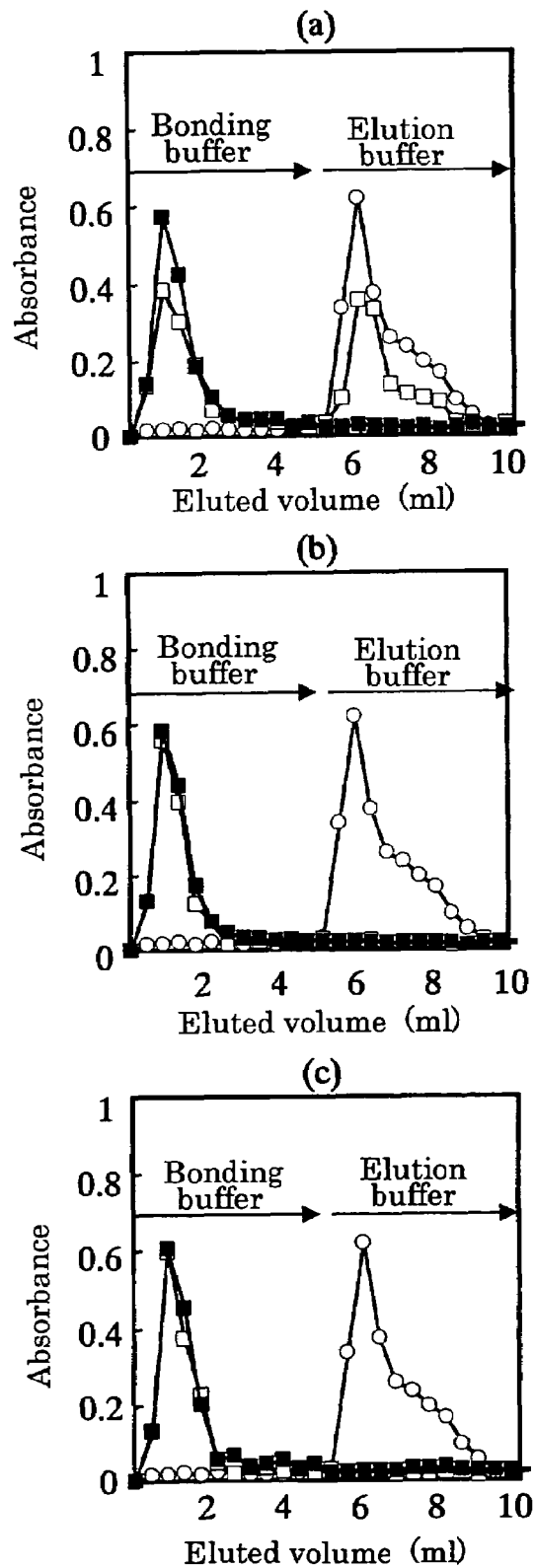
FIG. 14 is a diagram showing an elution profile of a PEG-grafted gelatin micelle solution from affinity column. (a), (b) and (c) show the cases of PEG portions having a molecular weight of 2000, 5000 and 12000, respectively. Sign ○ shows a grafted percentage of 0%, □ shows 85% and ■ shows 100%.

The results were shown in FIG. 14. From the results, it is considered that micelle in which gelatin was present in the core and PEG was present in the shell was formed irrespective of the molecular weight of PEG.

Example 25

In Vivo Internal Moving States of Various PEG-Grafted Gelatins

[Experimental Method]

The in vivo moving state of each of the various PEG-grafted gelatins prepared in Example 22 was studied in the following method.

50 mg of each PEG-grafted gelatin was dissolved in 1 ml of PBS (pH 7.4) and 10 μL of the resulting solution was subjected to $^{125}$I labeling by the chloramines T method. The labeled PEG-grafted gelatin was purified using a PD-10 column. To the gelatin, 990 μL of unradiolabeled PEG-grafted gelatin solution was added. 100 μL (5 mg) of this solution was administered by bolus injection from the mouse neck vein. After 1, 3, 6, 12 and 24 hours, the mouse was subjected to euthanasia and the radiation activity in the blood was determined by a γ-counter. The experimental results were calculated from the radiation activity of each organ by a method of Konishi et al. (Clinical Cancer Research, 2001).

[Results]

Figure 15:
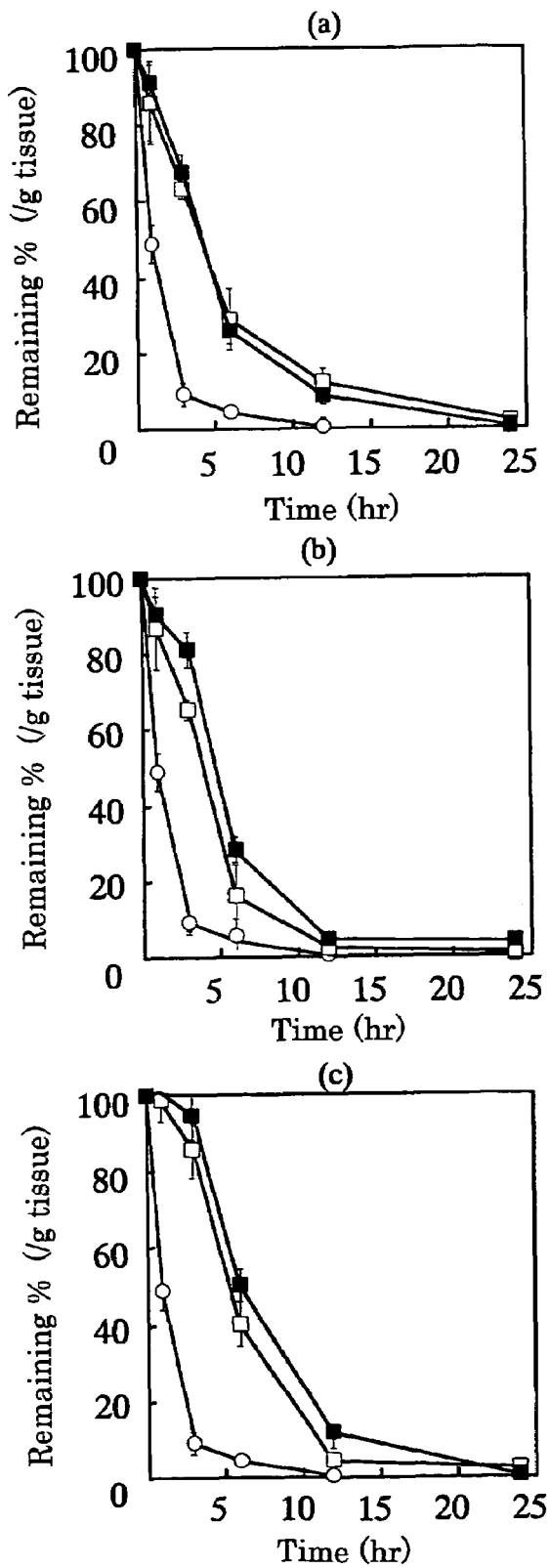
FIG. 15 is a diagram showing a pattern of decreasing gelatin or PEG-grafted gelatin in blood after intravenous injection. (a), (b) and (c) show the cases of PEG portions having a molecular weight of 2000, 5000 and 12000, respectively. Sign ○ shows a grafting ratio of 0%, □ shows 85% and ■ shows 100%.

The remaining rate of the gelatin in the blood was shown in FIG. 15.

Figure 16:
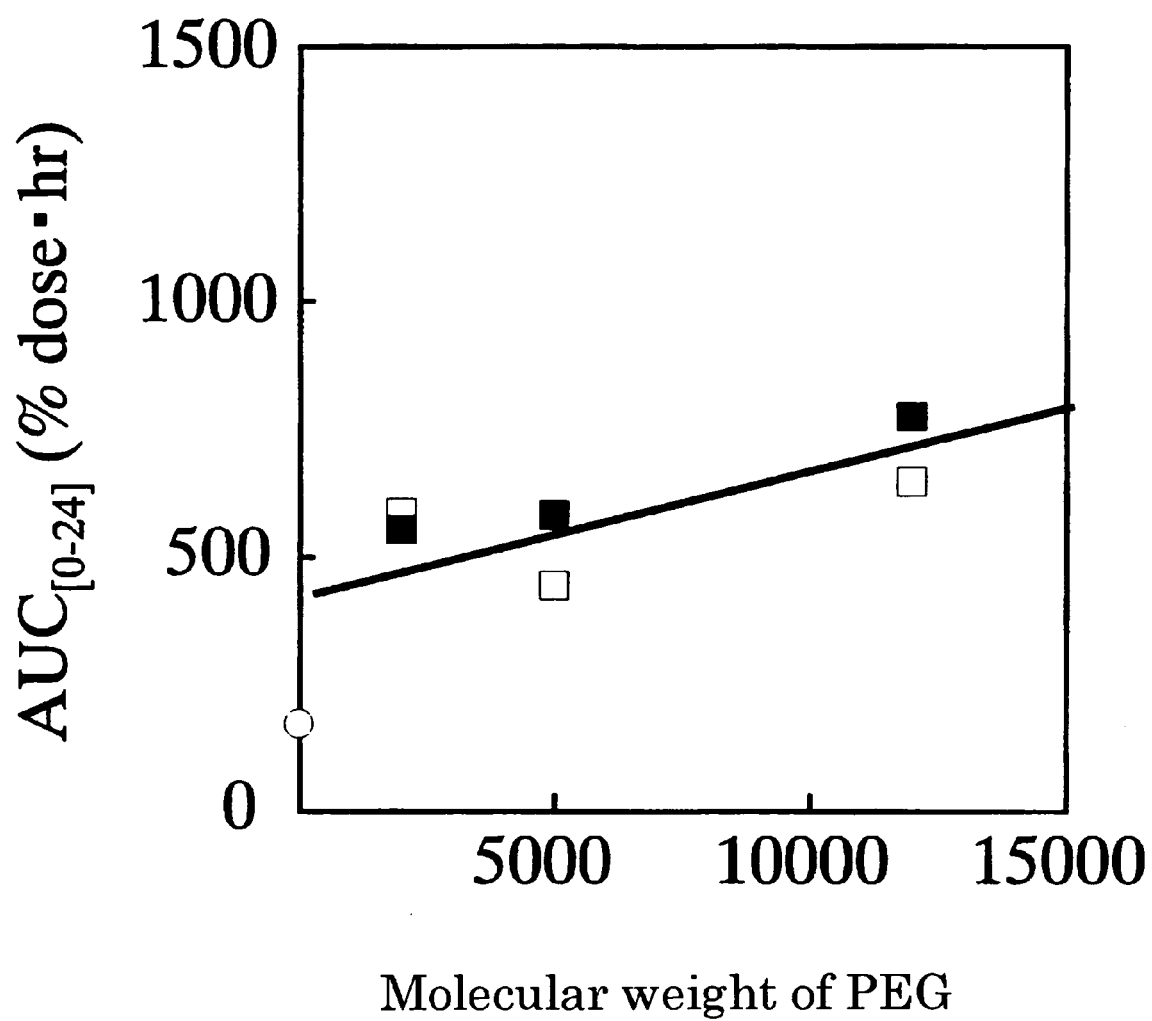
FIG. 16 is a diagram showing a relation of AUC and the molecular weight of a grafted PEG from 0 to 4 hours after injection. Sign ○ shows a grafting ratio of 0%, □ shows 85% and ■ shows 100%.

Furthermore, from the remaining patterns in the blood, the relation of the AUG and the PEG molecular weight for 0 to 24 hours was shown in FIG. 16.

[Consideration]

It is revealed from FIG. 15 that the life of the gelatin in blood is significantly prolonged by grafting the PEG. From FIG. 16, it is further considered that the AUG of the PEG-grafted gelatin shows a high value as compared with ungrafted gelatin and this fact is caused by the PEG chains present on the micelle surface.

Example 26

In Vitro Stability Test of PEG-Grafted Gelatin Derivative Micelle to Enzyme

[Experimental Method]

Of the various PEG-grafted gelatin derivatives prepared in Example 22, 50 mg of a gelatin derivative prepared by using 2-fold mols of PEG having a molecular weight of 5000 was dissolved in 1 ml of DDW (50 mg/mL). 500 μL of the resulting solution was added to 4.5 ml of each of a Japanese Pharmacopoeia first solution (pH 1.2), a second solution (pH 6.8), pepsin (10 U/mL)+first solution or trypsin (10 U/mL)+second solution and subjected to disintegration test. The test was carried out under the conditions based on Japanese Pharmacopoeia disintegration test. The decomposition of the gelatin was evaluated by carrying out SDS-PAGE of the sample prepared after the test. Further, 500 μL of the sample was added to 4.5 mL of DDW to prepare a control group.

[Results]

With regard to the PEG-grafted gelatin, in any of the control group, the first solution, the second solution, pepsin+the first solution and trypsin+the second solution, a lowering of the gelatin molecular weight was not confirmed.

Comparative Example 1

50 mg of gelatin, which was not subjected to PEG grafting, was dissolved in 1 ml of DDW. 500 μL of the resulting solution was added to 4.5 mL of each of DDW, first solution, second solution, pepsin+first solution and trypsin+second solution, respectively, and then, subjected to disintegration test. The test was carried out under the conditions based on Japanese Pharmacopoeia disintegration test. The decomposition of the gelatin was evaluated by carrying out SDS-PAGE of the sample prepared after the test.

[Results]

In the gelatins, which were not subjected to PEG grafting, except for the control group and the second solution, a lowering of the gelatin molecular weight was confirmed.

[Consideration]

These results show that forming the micelle structure that PEG chains are present on the surface, hydrolysis of the gelatin under the acidic conditions of pH 1.2 can be depressed and the resistance of the gelatin to the enzyme decomposition caused by pepsin, trypsin, etc., is improved. For example, it is considered that these properties can be used as an enteric coating material for drugs capable of protecting the drugs from hydrolysis of acids and enzymes by enclosing the drugs in the micelle. This shows a new conception of the micelle type enteric coating materials different from capsulation or coating of drugs by known enteric polymer materials.

Example 27

Preparation of Gelatin Derivative Grafted with Lactic Acid Oligomer (1) Preparation of L-Lactic Acid Oligomer ($LLA_0$)

[Experimental Method]

20 g (0.138 mol) of L-lactide (manufactured by PURAC Co.) was fed to a 100 mL round bottom flask and deaerated by a vacuum pump and dried over night. The flask was purged with nitrogen and thereafter, $\frac{1}{10}$ mol equivalent weight of 2-(2-methoxyethoxy)ethanol was added based on L-lactide and heated to 130° C. After the fusion of L-lactide, $\frac{1}{100}$ mol equivalent weight of tin octylate ($SnOct_2$) previously prepared as a 0.1 g/mL toluene solution was added based on the amount of L-lactide and then reaction was started. The reaction was carried out at 130° C. for 4 hours in a stream of nitrogen. After completion of the reaction, the reactant was dissolved in 100 mL of tetrahydrofuran (THF). Insoluble components were removed by centrifugation, and supernatant was added dropwise to 500 mL of cold water to precipitate again. The precipitate was recovered by centrifugation. The resulting precipitate was dissolved again in 200 mL of ethyl acetate. To the solution, magnesium sulfate was added and dried overnight, and thereafter filtered off. The remainder was concentrated under reduced pressure by a rotary evaporation. The precipitated specimen was dissolved again in THF, and re-precipitated in cold water. The precipitate was washed and recovered by centrifugation followed by drying in vacuum.

(2) Evaluation of Polymerization Degree (DP) of $LLA_0$

[Experimental Method]

$^1$H-NMR measurement was carried out using $CDCl_3$ as a solvent. From the ratio of the integral value of a peak at 3.38 ppm and the integral value of a peak at 1.41 to 1.63 ppm of the obtained spectrum, a polymerization degree was determined.

[Results]

From the determination, DP was 14.7 and Mn was 1000. In FIG. 17, the structural formula of $LLA_0$ and the $^1$H-NMR spectrum were shown.

(3) Preparation of Gelatin Derivatives Grafted with $LLA_0$

[Experimental Method]

Gelatin (manufactured by Nitta gelatin Inc.; derived from beef bones; molecular weight 100000; isoelectric point 5) was dissolved in dimethylsulfoxide (DMSO) so that the resulting solution has a concentration of 0.02 mg/mL. Separately, DMSO solutions were prepared in an amount of 25 mL in such a way that $LLA_0$ was dissolved in a weight ratio based on amino group of the gelatin of 5:28, 10:28, 20:28 and 30:28. To each of the $LLA_0$/DMSO solutions, equimolar amounts of N,N'-disuccinimidyl carbonate (DSC) and 4-dimethyl aminopyridine (DMAP) were added and subjected to reaction at 40° C. for 6 hours. Thereafter, to the reaction solution, 25 mL of the gelatin/DMSO solution was added while stirring and subjected to reaction at 40° C. for 12 hours. The DMSO was previously dehydrated using Molecular sieve 3A and then submitted to use. After the reaction, the reactant was dialyzed against ultra pure water using a cellulose tube (fractionation molecular weight 12000 to 14000). From starting the dialysis, the ultra pure water was changed after 1, 2, 4, 8, 12, 24, 36 and 48 hours, and thereby DMSO was removed. Unreacted $LLA_0$ precipitated was removed by centrifugation and the supernatant was lyophilized. The resulting compound (gelatin-$LLA_0$) was kept with drying in vacuum until use.

(4) Evaluation of Grafted Gelatin Derivatives

[Experimental Method]

With regard to each gelatin-$LLA_0$ prepared, determination of amino group was carried out to evaluate the percentage of grafting $LLA_0$ to the gelatin. The determination of amino group was carried out by the TNBS method. Namely, using an isotonic phosphate buffer with a pH of 7.4, 1 mL of a 4% (w/v) aqueous sodium hydrogen carbonate solution was added to 1 mL of the gelatin-$LLA_0$ aqueous solution having a concentration of 0.5 mg/mL. Further, 1 mL of 0.1% (w/v) 2,4,6-trinitrobenzene sodium sulfonate (TNBS) was added and subjected to reaction at 40° C. for 2 hours. After the reaction, the absorbance of a resulting yellow-colored aqueous solution was measured at a wave-length of 415 nm. Using β-alanine as a standard specimen, a calibration curve was made and the grafting ratio was determined from the calibration curve.

[Results]

The numbers of amino groups of the gelatin and the gelatin-$LLA_0$ were determined by the TNBS method. In the gelatin, amino groups of 28 residues were present per molecule. On the other hand, in the gelatin-$LLA_0$, a decrease in amino groups was observed. Each grafting ratio was determined as shown in FIG. 1.

TABLE 1

Charging ratio of $LLA_0$ to amino group of gelatin and Grafting percentage

| | Charging ratio[a] (%) | Grafting ratio[b] |
|---|---|---|
| Gelatin-$LLA_0$ (5) | 5:28 (17.9) | 10.3 |
| Gelatin-$LLA_0$ (10) | 10:28 (35.7) | 34.1 |
| Gelatin-$LLA_0$ (20) | 20:28 (71.4) | 56.7 |
| Gelatin-$LLA_0$ (30) | 30:28 (107.1) | 61.3 |

[a] A molar ratio of $LLA_0$ added for grafting to amino groups of the gelatin.
[b] Mol % of grafted $LLA_0$ to amino groups of the gelatin.

[Consideration]

The terminal hydroxyl group of $LLA_0$ was activated by DSC and thereby the reaction to amino groups of the gelatin could be conducted. By changing the charging ratio of $LLA_0$ to amino groups of the gelatin, grafted gelatin derivatives having different grafting percentages could be prepared. In the specimen having a relatively small charging ratio, the grafting ratio was increased in accordance with the charging ratio. However, in the specimen having a large charging ratio, when the grafting ratio was a small value of 50 to 60%, saturation was caused contrary to our expectations. Steric hindrance of graft chain is considered as one of the causes.

Example 28

$LLA_0$-PEG-Grafted Gelatin Derivatives (1) Grafting of PEG to $LLA_0$ Grafted Gelatin Derivative

[Experimental Method]

$LLA_0$ grafted gelatin prepared in Example 27 (3) was dissolved in DMSO so that the solution had a concentration of 5% (w/w). Further, SUNBRIGHT MEC-50HS (manufactured by NOF CORPORATION; molecular weight 5330) was dissolved in DMSO. The concentration of SUNBRIGHT MEC-50HS was 2-fold mols that of amino groups present in the gelatin. DMSO was previously dehydrated using molecular sieve 3A and submitted to use.

1 ml of a solution of SUNBRIGHT MEC-50HS in limited amounts was added to 2 ml of the $LLA_0$ grafted gelatin solution with stirring and reacted at room temperature for 3 hours.

After the reaction, the reactant was dialyzed against ultra pure water using a cellulose tube (fractionation molecular weight 12000 to 14000). From starting the dialysis, the ultra pure water was changed after 1, 2, 4, 8, 12, 24, 36 and 48 hours, and thereby DMSO and unreacted SUNBRIGHT MEC-50HS, those obtained by replacing succinimidyl succinate with carboxyl group, succinimidyl group eliminated substances were completely removed. The resulting compound ($LLA_0$-PEG-grafted gelatin) was lyophilized and kept at −20° C. until use.

(2) Solubilizing of Paclitaxel by $LLA_0$-PEG-Grafted Gelatin

[Experimental Method and Results]

(a)

A 10 mg/ml ethanol solution of paclitaxel was prepared as (a PTX solution). A 2% aqueous solution of $LLA_0$-PEG-grafted gelatin was prepared as a grafted gelatin solution. 30 μL of the PTX solution and 500 μL of the grafted gelatin solution were mixed to prepare a blue white micelle solution.

(b)

30 μL of the PTX solution and 500 μL of water were mixed with stirring to cause white precipitation.

(c)

A 2% gelatin aqueous solution was prepared as a gelatin solution. 30 μL of the PTX solution and 500 μL of the gelatin solution were mixed with stirring to cause white precipitation.

Example 29

Sheet Containing PEG-Grafted Gelatin Derivative (1) Preparation of Gelatin Derivative Grafted by PEG A gelatin derivative grafted by PEG was prepared by the same method as in Example 1.

(2) DSC Measurement of PEG-Grafted Gelatin

Figure 18:
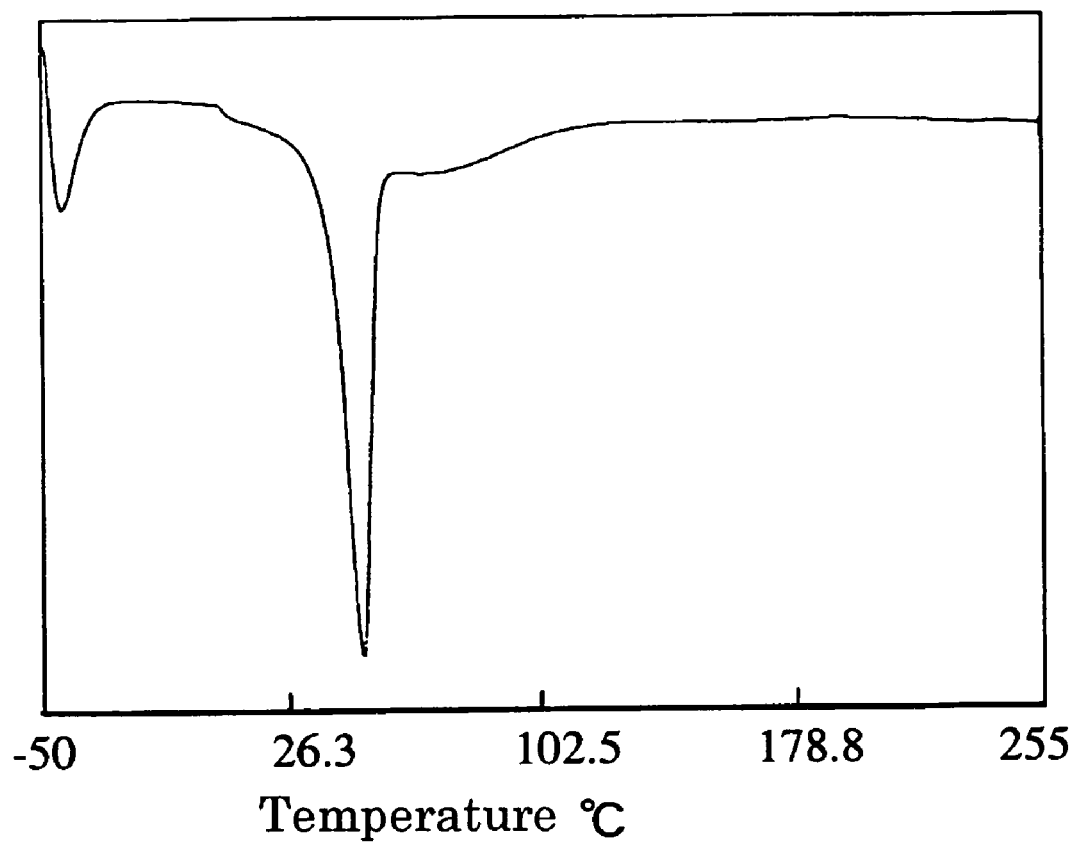
FIG. 18 is a diagram showing a DSC curve of a PEG-grafted gelatin derivative.

The thermal analysis of the PEG-grafted gelatin prepared in (1) was measured by DSC under the following conditions.
Type: DSC210 manufactured by Seiko Instruments Inc.
Measurement temperature: −30° C. to 250° C., 10° C./min
Temperature elevating conditions: 10° C./min
The measurement results of DSC were shown in FIG. 18.

(3) Method for Preparing Specimen Used in Evaluation on In Vivo Absorption 1 g of gelatin (manufactured by Nitta Gelatin Inc.; derived from beef bones; molecular weight 100000; isoelectric point 5) and 1 g of the PEG-grafted gelatin were dissolved in 10 mL of purified water while heating. Each 200 μl of this resulting solution was put on a glass plate and allowed to stand at 4° C. for 12 hours and thereby sufficiently gelatinized, followed by lyophilization. The resulting gel was cross-linking treated by heating at 160° C. under reduced pressure in vacuum for 0, 3, 6, 12 or 24 hours, to prepare specimens having different cross-linking degrees for evaluating the in vivo absorption.

(4) Method of Testing In Vivo Absorption

The specimen for evaluating in vivo absorption prepared in accordance with the method (3) was packed in a small polypropylene container. Near back lumbar part of a 8-week old male ddy mouse was incised perpendicular to the median line in a length of about 2 cm. The specimen packed in the container was embedded in the skin from the cut part and the cut part was sewed up. The mouse having the specimen embedded was kept from the next day for 5 days. Thereafter, the presence or absence of the embedded specimen was judged by incision again.

(5) Test Results on In Vivo Absorption

With regard to the gelatin and the PEG-grafted gelatin, the test on in vivo absorption was carried out in accordance with the above-mentioned method (4). The results were shown in Table 2.

TABLE 2

Results of test for in vivo absorption

| | Cross-linking time | | | | |
|---|---|---|---|---|---|
| | 0 | 3 | 6 | 12 | 24 |
| Specimen from PEG-grafted gelatin | − | − | ± | + | + |
| Specimen from gelatin | − | + | + | ++ | ++ |

−: Specimen was not observed.
±: Traces was observed.
+: Specimen was observed.
++: Original specimen was observed.

As is clear from Table 2, the specimen prepared by cross-linking treating the PEG-grafted gelatin with heating at 160° C. for 3 hours was completely disappeared after five days. The specimen prepared by cross-linking treating the PEG-grafted gelatin with heating for 6 hours or more was remained almost in the original state after five years. After the operation of abdominal cavity and serous membrane, the recovery period was about 5 days. Therefore, it is found that the specimen prepared using the PEG-grafted gelatin can attain almost ideal absorption.

In the meantime, as is clear from Table 2, the specimen prepared by gelatin not subjected to heat treatment at 160° C. was completely absorbed within 5 days. The specimen prepared by gelatin subjected to heat treatment at 160° C. for 3 hours or more was remained in the almost original state after 5 days. From these results, it is presumed that it is difficult to control the gelatin absorption by cross-linking and further it is difficult to prevent adhesion by using the gelatin specimen not subjected to derivatization.

(6) Method of Preparing Sheet for Evaluating Adhesion Test after Operation 1 g of the gelatin or the PEG-grafted gelatin derivative was dissolved in 10 mL of purified water with heating. The polymer solution was injected into a PFA made laboratory dish and allowed to stand at 4° C. for 12 hours to conduct gelation sufficiently. The resulting gel was lyophilized and then cross-linking treated with heating at 160° C. for 3 hours under reduced pressure in vacuum.

(7) Method of Adhesion Test after Operation

7-Week old 4 female wister rats were used. For each rat, the hypogastric region was shaved and disinfected and thereafter incised in median line in a length of about 2 cm. The fatty tissue surrounding the uterus was cut off to expose right and left uterus channels. The channels were subjected to scrap abrasion 10 times using an iodine tincture impregnated defatted cotton. For 4 rats, on the left and right uterine horns, the sheet prepared by using the gelatin or the PEG-grafted gelatin in accordance with the method (6) for evaluating the adhesion test after operation was adhered and the peritoneum and the skin were sewed to close them. After 15 days, laparotomy was conducted again and the adhesion degree was evaluated on the light and right uterine horns. In the adhesion degree evaluation with score judgment, the number 0 expresses no adhesion, the number 1 expresses very light adhesion such that loss of blood was not caused in peeling on the uterus channel surface, and the number 3 expresses severe adhesion accompanied with inflammation. The average value thereof is expressed as a degree of adhesion.

(8) Results of Adhesion Test after Operation

With regard to the sheet prepared by using the gelatin or the PEG-grafted gelatin for evaluating the adhesion test after the operation, the effect of adhesion after the operation was tested in accordance with the method (7). As a sham operated group, with regard to four rats, the surfaces of the left and right uterine horns were only subjected to treatment with iodine tincture and the sheet for evaluating the adhesion test was not adhered thereon. After 15 days, the degree of the adhesion was evaluated on the left and right uterine horns.

The results are shown in Table 3.

TABLE 3

Results of adhesion test after operation

| | Adhesion score |
|---|---|
| Sheet prepared from PEG-grafted gelatin | 0 |
| Sheet prepared from gelatin | 3 |
| Sham operated group | 2 |

As is clear from Table 3, the sheet prepared from PEG-grafted gelatin was not observed in the left and right uterine horns, and the uterine serous membrane was normally cured and no adhesion to the surrounding adipose tissue was confirmed.

In the meantime, the sheet prepared from the gelatin was remained in the original state on each of the left and right uterine horns and the surroundings thereof show sever foreign-body reaction. Further, considerable amounts of hematoma were caused on the covering inside and thereby normal curing was chronically delayed with complicating inflammation.

In the sham-operated group, adhesion with the surrounding adipose tissue or light adhesion with peritoneum sewing was observed scatteredly.

Example 30

Evaluation of Adhesion Property of PEG-Grafted Gelatin (1) Method of Preparing Specimen for Evaluating Macrophage Adhesion Property 1 g of gelatin or a derivative thereof was dissolved in 10 mL of purified water while heating. This resulting polymer solution was injected into a PFA made laboratory dish and allowed to stand at 4° C. for 12 hours to conduct gelation sufficiently. The resulting gel was lyophilized and then subjected to cross-linking treatment with heating at 160° C. for 3 hours under reduced pressure in vacuum.

(2) Test Method of Macrophage Adhesion Property

First, to 10-week old female ddy mouse, 2 ml of a previously sterilized Brewer's thioglycolate medium (manufactured by Difco Co.) was administered to intraperitoneal. After 5 days, the mouse was killed with blood-letting and 5 ml of PBS(−) cooled at 4° C. was administered intraperitoneal. After 5 minutes, about 4 ml of intraperitoneal effusion was recovered and was centrifuged at 8000 revolution/min for about 5 minutes to prepare a cell mass of effused macrophage. To the cell mass, 2 ml of RPMI1640 medium containing 10% FCS was added and sufficiently suspended.

Next, a specimen prepared in accordance with "the method of preparing the specimen for evaluating adhesion of macrophage" according to the above-mentioned (1) was sufficiently swelled with a RPMI1640 medium to prepare a specimen for evaluating the adhesion property of macrophage. The specimen was inserted to a 24 wells culture plate and thereby the macrophage suspension with each 1 ml portion was put. The specimen was cultured at 37° C. in 5% $CO_2$ for 24 hours. To the specimen, 1% glutaraldehyde was added and fixed at a low temperature for 1 hour. Thereafter, the specimen was dehydrated with ethanol, purged with t-butyl alcohol and lyophilized. Surface observation was carried out by a scanning electron microscope (Hitachi Type S-3000N) and the adhesion of macrophage was evaluated.

(3) Preparation of PEG-Grafted Gelatin

The PEG-grafted gelatin was prepared by the same method as in Example 1.

(4) Method of Preparing Macrophage Non-Adhesion Specimen

Using the PEG-grafted gelatin synthesized in the same manner as in (3), a specimen cross-linking treated with heating for evaluating adhesion was prepared in accordance with the preparation method of a specimen for evaluating macrophage adhesion property as described in the above-mentioned (1).

(5) Test of Macrophage Adhesion Property

The test of adhesion property was carried out in accordance with the test method of macrophage adhesion property as described in the method (2).

On one piece of the PEG-grafted gelatin, the effused macrophage suspension was put and the surface of the material cultured for 24 hours was fixed and dehydrated, and thereafter observed under conditions of no vapor deposition by a low vacuum scanning electron microscope. The results were shown in FIG. 19(A). From the results, cell was not confirmed at all on the surface of the PEG derivative of gelatin crosslinked with heating at 160° C. for 3 hours. It is considered that the PEG-grafted gelatin does not provide scaffold to macrophage having high adhesion. The foreign-body reaction to embedded materials brings persisting inflammation or fiberization and has many clinical harmful effects. In this foreign-body reaction, the adhesion of the effusing macrophage to the material surface is decreased prior to forming polynuclear mega cells which play a main role such as inflammation mediator production. This fact is a very favorable property as anti-adhesive membranes after operation or materials for in vivo embedding.

(6) Comparative Example 2

Gelatin

[Method of Preparing Specimen for Macrophage Non-Adhesion]

Using gelatin prepared before PEG grafting treatment (manufactured by Nitta Gelatin Inc.; derived from beef bones; molecular weight 100000; isoelectric point 5), a specimen for in vivo absorbing property was prepared by cross-linking treatment with heating in accordance with the method of preparing a specimen for evaluating macrophage adhesion property as described in the method (1).

[Test of Macrophage Adhesion Property]

The test of adhesion property was carried out in accordance with "the test method of macrophage adhesion property" as mentioned in the above (2).

On small piece of crosslinked gelatin, an effusion macrophage suspension was put and cultivated for 24 hours. The material surface was fixed and dehydrated, and then was observed in conditions of no evaporating by a low vacuum scanning electron microscope. The results were shown in FIG. 19(B). As is clear from the results, it is revealed that the surface of the gelatin crosslinked with heating at 160° C. for 3 hours is tightly covered with the cells such as macrophage, etc. It is considered that this state shows the initial process of capsulization for embedding materials. In vivo, the injection of inflammation mediator and migration of fibroblast further promote capsulization. As described in the above, it is considered that when the heat crosslinked gelatin is embedded in vivo, it makes the foreign-body reaction worse and therefore it was not favorable as an anti-adhesive membrane after operation.

INDUSTRIAL APPLICABILITY

The gelatin derivatives of the present invention are stable and form high-molecular weight micelle having a small average particle diameter. The high-molecular weight micelle is favorably used for DDS as a carrier of drugs. Because the high-molecular weight micelle has a very small CMC, the high-molecular weight micelle formed is stable in the blood even if intravenous administration that it is rapidly diluted after in vivo administration. Further, because the average particle is small different from conventional particles of μm order, it is considered that RES or embolus can be avoided after administration in the blood, the high-molecular weight micelle can reach to the depth of lung after endotracheal administration or the dose of drugs sufficient for cure can be administered by an extremely minute amount of the solution. Independent from their molecular size, the high-molecular weight micelle of the present invention can stably enclose drugs, for example, peptide prepared from low molecular drugs, high-molecular drugs such as protein etc., polysaccharides, drugs comprising nucleic acid (such as DNA, RNA, antisense DNA, decoy nucleic acid, etc.) or the like.

The gelatin derivatives and their micelle of the present invention are also effective for not only the drugs but also DDS carriers used for diagnosis, prevention drugs, substances in cosmetics and stabilization thereof.

Furthermore, they can be used as medical materials such as anti-adhesive membrane materials utilizing their anti-adhesion property to inflammation cells.

Moreover, they can be used as enteric coating agents at oral administration utilizing the property capable of guarding drugs from hydrolysis caused by acids or enzymes. That is, the micelle system of the present invention realizes enteric coating technique of emulsion type drugs.

The invention claimed is:

1. A high-molecular weight micelle which comprises a gelatin derivative that is gelatin covalently bonded to organic compounds, wherein the organic compounds, before covalently bonding with the gelatin, are:
   (i) at least one compound selected from the group consisting of an alkyldiamine, an alkyldicarboxylic acid, and an aminoalkylcarboxylic acid, and (ii) a polyethylene glycol derivative represented by the following formula (1):

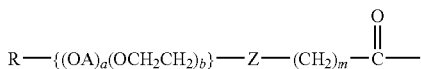
(1)

wherein R is a straight or branched alkyl group or alkenyl group both having 1 to 24 carbon atoms, OA is an oxyalkylene group having 3 to 4 carbon atoms, the oxyalkylene group and an oxyethylene group may be added in the block state or randomly, a and b are respectively an average addition mole number of oxyalkylene group and that of the oxyethylene group, and satisfy the following formulas; $0 \leq a \leq 200$, $4 \leq b \leq 2000$, and $a/(a+b) \leq 0.5$, Z is O or OC(O) and m is an integer of 0 to 3, and the micelle has a grain diameter of 20 to 500 nm.

2. A high-molecular weight micelle which comprises a gelatin derivative which is gelatin covalently bonded to organic compounds, wherein the organic compounds covalently bonded to the gelatin are succinic acid and a polyethylene glycol derivative represented by the following formula (1):

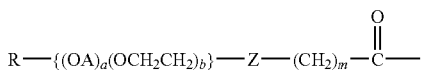
(1)

wherein R is a straight or branched alkyl group or alkenyl group both having 1 to 24 carbon atoms, OA is an oxyalkylene group having 3 to 4 carbon atoms, the oxyalkylene group and an oxyethylene group may be added in the block state or randomly, a and b are respectively an average addition mole number of oxyalkylene group and that of the oxyethylene group, and satisfy the following formulas; $0 \leq a \leq 200$, $4 \leq b \leq 2000$, and $a/(a+b) \leq 0.5$, Z is O or OC(O) and m is an integer of 0 to 3, and the micelle has a grain diameter of 20 to 500 nm.

3. A high-molecular weight micelle which comprises a gelatin derivative which is gelatin covalently bonded to organic compounds, wherein the organic compounds covalently bonded to the gelatin are ethylene diamine and a polyethylene glycol derivative represented by the following formula (1):

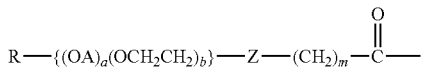
(1)

wherein R is a straight or branched alkyl group or alkenyl group both having 1 to 24 carbon atoms, OA is an oxyalkylene group having 3 to 4 carbon atoms, the oxyalkylene group and an oxyethylene group may be added in the block state or randomly, a and b are respectively an average addition mole number of oxyalkylene group and that of the oxyethylene group, and satisfy the following formulas; $0 \leq a \leq 200$, $4 \leq b \leq 2000$, and $a/(a+b) \leq 0.5$, Z is O or OC(O) and m is an integer of 0 to 3, and the micelle has a grain diameter of 20 to 500 nm.

4. The high-molecular weight micelle according to claim 1, wherein the organic compounds are an alkyldiamine and the polyethylene glycol derivative.

5. The high-molecular weight micelle according to claim 1, wherein the organic compounds are an alkyldicarboxylic acid and the polyethylene glycol derivative.

6. The high-molecular weight micelle according to claim 1, wherein the organic compounds are an aminoalkylcarboxylic acid and the polyethylene glycol derivative.

* * * * *